US011980658B2

(12) United States Patent
O'Hehir et al.

(10) Patent No.: US 11,980,658 B2
(45) Date of Patent: *May 14, 2024

(54) IMMUNOTHERAPEUTIC MOLECULES AND USES THEREOF

(71) Applicant: ARAVAX PTY LTD, Melbourne (AU)

(72) Inventors: Robyn O'Hehir, Parkville (AU); Jennifer Rolland, Toorak (AU); Sara Prickett, Elwood (AU)

(73) Assignee: ARAVAX PTY LTD, Melbourne (AU)

( * ) Notice: Subject to any disclaimer, the term of this patent is extended or adjusted under 35 U.S.C. 154(b) by 76 days.

This patent is subject to a terminal disclaimer.

(21) Appl. No.: 17/374,519

(22) Filed: Jul. 13, 2021

(65) Prior Publication Data
US 2022/0088159 A1 Mar. 24, 2022

Related U.S. Application Data

(63) Continuation of application No. 14/440,025, filed as application No. PCT/AU2013/001255 on Oct. 30, 2013, now Pat. No. 11,096,994.

(30) Foreign Application Priority Data

Oct. 30, 2012 (AU) ............................... 2012904780

(51) Int. Cl.
A61K 39/00 (2006.01)
A61K 38/00 (2006.01)
A61K 38/04 (2006.01)
A61K 38/10 (2006.01)
A61K 39/35 (2006.01)
G01N 33/50 (2006.01)

(52) U.S. Cl.
CPC ............ A61K 39/001 (2013.01); A61K 38/00 (2013.01); A61K 38/04 (2013.01); A61K 38/10 (2013.01); A61K 39/35 (2013.01); G01N 33/5005 (2013.01); A61K 2039/57 (2013.01)

(58) Field of Classification Search
None
See application file for complete search history.

(56) References Cited

U.S. PATENT DOCUMENTS

| 5,558,869 | A | 9/1996 | Burks, Jr. et al. |
| 5,973,121 | A | 10/1999 | Burks, Jr. et al. |
| 6,835,824 | B1 | 12/2004 | Burks, Jr. et al. |
| 7,179,645 | B2 | 2/2007 | Humphreys et al. |
| 7,923,209 | B2 | 4/2011 | Spertini et al. |
| 8,815,249 | B2 | 8/2014 | Humphreys et al. |
| 9,289,487 | B2 | 3/2016 | Humphreys et al. |
| 11,096,994 | B2 | 8/2021 | O'Hehir et al. |
| 11,266,737 | B2 | 3/2022 | O'Hehir et al. |
| 2002/0147140 | A1 | 10/2002 | Rosen et al. |
| 2003/0202980 | A1 | 10/2003 | Caplan et al. |
| 2003/0235594 | A1 | 12/2003 | Humphreys et al. |
| 2004/0058881 | A1 | 3/2004 | Humphreys et al. |
| 2006/0002947 | A1 | 1/2006 | Humphreys et al. |
| 2006/0292138 | A1 | 12/2006 | Chen |
| 2008/0305122 | A1 | 12/2008 | Humphreys et al. |
| 2010/0291145 | A1 | 11/2010 | Humphreys et al. |
| 2011/0294700 | A1 | 12/2011 | Thelen et al. |
| 2012/0178139 | A1 | 7/2012 | Hubbell et al. |
| 2015/0328294 | A1 | 11/2015 | O'Hehir et al. |
| 2016/0243253 | A1 | 8/2016 | Fraser et al. |
| 2016/0279234 | A1 | 9/2016 | Kishimoto et al. |
| 2016/0375130 | A1 | 12/2016 | O'Hehir et al. |
| 2022/0280637 | A1 | 9/2022 | O'Hehir et al. |

FOREIGN PATENT DOCUMENTS

| CN | 102533781 A | 7/2012 |
| CN | 102816232 A | 12/2012 |
| EA | 019923 B1 | 7/2014 |
| EP | 2153841 A1 | 2/2010 |
| GB | 2455108 A | 6/2009 |
| JP | 2002509117 A | 3/2002 |
| JP | 2006515744 A | 6/2006 |
| JP | 2013040138 A | 2/2013 |
| RU | 2285042 C2 | 10/2006 |
| RU | 2429881 C2 | 9/2011 |
| WO | 1997024139 A1 | 7/1997 |
| WO | 1999034826 A1 | 7/1999 |
| WO | 1999036090 A1 | 7/1999 |
| WO | 1999038978 A1 | 8/1999 |

(Continued)

OTHER PUBLICATIONS

Hu, et al.; Prediction of Secondary Structure and B Cell Epitopes of Peanut Allergen Ara H 2.02; Food Science; 2009; vol. 30, No. 21; pp. 13-15.
Akdis, et al., "Bypassing IgE and Targeting T Cells for Specific Immunotherapy of Allergy", Trends in Immunology, vol. 22, No. 4, May 2001, pp. 175-178.
Akdis, et al., "Mechanisms and Treatment of Allergic Disease in the Big Picture of Regulatory T Cells", Journal of Allergy and Clinical Immunology, Apr. 2009, 123(4):735-746.
Akdis, et al., "Mechanisms of Allergen-Specific Immunotherapy", Allergy, vol. 55, 2000, pp. 522-530.
Akdis, et al., "Mechanisms of Allergen-Specific Immunotherapy", Journal of Allergy and Clinical Immunology, Jan. 2011, 127(1):18-27.

(Continued)

Primary Examiner — Nora M Rooney
(74) Attorney, Agent, or Firm — Kilpatrick Townsend & Stockton LLP

(57) ABSTRACT

The present invention relates generally to molecules such as peptides, polypeptides and proteins which interact immunologically with T lymphocytes in subjects having peanut allergy, or allergy to other tree nuts, and genetic sequences encoding same. These molecules are preferably immunointeractive with T cells in subjects having an allergy to the Ara h 1 allergen. The molecules of the present invention are useful in the development of diagnostic, therapeutic and prophylactic agents for conditions characterised by an aberrant, inappropriate or otherwise unwanted immune response to Ara h 1 or derivative or homologue thereof.

18 Claims, 11 Drawing Sheets
Specification includes a Sequence Listing.

(56) References Cited

FOREIGN PATENT DOCUMENTS

| WO | 1999045961 A1 | 9/1999 |
|---|---|---|
| WO | 0052154 A2 | 9/2000 |
| WO | 0054803 A2 | 9/2000 |
| WO | 2000051647 A2 | 9/2000 |
| WO | 2001039799 A2 | 6/2001 |
| WO | 2001040264 A2 | 6/2001 |
| WO | 02040676 A2 | 5/2002 |
| WO | 2002074250 A2 | 9/2002 |
| WO | 02088317 A2 | 11/2002 |
| WO | 02088367 A1 | 11/2002 |
| WO | 2003047618 A2 | 6/2003 |
| WO | 2004081028 A2 | 9/2004 |
| WO | 2005121166 A1 | 12/2005 |
| WO | 2008145998 A1 | 12/2008 |
| WO | 2008146003 A1 | 12/2008 |
| WO | 2009022154 A2 | 2/2009 |
| WO | 2009022155 A2 | 2/2009 |
| WO | 2009022156 A2 | 2/2009 |
| WO | 2009022157 A2 | 2/2009 |
| WO | 2010000873 A1 | 1/2010 |
| WO | 2010018378 A2 | 2/2010 |
| WO | 2010018384 A1 | 2/2010 |
| WO | 2010/109010 A1 | 9/2010 |
| WO | 2011032097 A1 | 3/2011 |
| WO | 2011106645 A1 | 9/2011 |
| WO | 2012/129246 A2 | 9/2012 |
| WO | 2013/036295 A1 | 3/2013 |
| WO | 2013/036296 A1 | 3/2013 |
| WO | 2013/104804 A2 | 7/2013 |
| WO | 2013/187906 A1 | 12/2013 |
| WO | 2014/066939 A1 | 5/2014 |
| WO | 2014/067993 A1 | 5/2014 |
| WO | 2014/138824 A1 | 9/2014 |
| WO | 2015/042664 A1 | 4/2015 |

OTHER PUBLICATIONS

Akdis, et al., "Therapeutic Manipulation of Immune Tolerance in Allergic Disease", Nature Reviews Drug Discovery, Aug. 2009, 8(8):645-660.

Alexander, et al., "Fel d 1-Derived T Cell Peptide Therapy Induces Recruitment of CD4+ CD25+; CD4+ Interferon-Gamma+ T Helper Type 1 Cells to Sites of Allergen-Induced Late-Phase Skin Reactions in Cat-Allergic Subjects", Clinical & Experimental Allergy, Jan. 2005, 35(1):52-58.

Alexander, et al., "The Effect of Fel d 1-Derived T-Cell Peptides on Upper and Lower Airway Outcome Measurements in Cat-Allergic Subjects", Allergy, Oct. 2005, 60(10):1269-1274.

Allen, et al., "The Evolution of Oral Immunotherapy for the Treatment of Peanut Allergy", Clinical & Experimental Allergy, Sep. 2011, 41(9):1172-1174.

Allergen Nomenclature, International Union of Immunological Societies (IUIS) Allergen Nomenclature Sub-committee. Available at: http://www.allergen.org/Allergen.aspx. Accessed Apr. 22, 2012, 12 pages.

Amann, et al., "Tightly Regulated Tac Promoter Vectors Useful for the Expression of Unfused and Fused Proteins in *Escherichia coli*", Gene, Sep. 30, 1988, 69(2):301-315.

Anagnostou, et al., "Efficacy and Safety of High Dose Peanut Oral Immunotherapy with Factors Predicting Outcome", Clinical & Experimental Allergy, Sep. 2011, 41(9):1273-1281.

Apostolou, et al., "Anaphylaxis to Gelofusine® Confirmed by in Vitro Basophil Activation Test: A Case Series", Anaesthesia, Apr. 2006, 61(3):264-268.

Asarnoj, et al., "IgE to Peanut Allergen Components: Relation to Peanut Symptoms and Pollen Sensitization in 8-Year-Olds", Allergy, Sep. 2010, 65(9):1189-1195.

Attwood et al. "The Babel of Bioinformatics", Science 290(5491):471-473.

Avery, et al., "Assessment of Quality of Life in Children with Peanut Allergy", Pediatric Allergy and Immunology, vol. 14, Issue 5, Oct. 2003, pp. 378-382.

Baldari, et al., "A Novel Leader Peptide which Allows Efficient Secretion of a Fragment of Human Interleukin 1 beta in *Saccharomyces cerevisiae*", The EMBO Journal, Jan. 1987, 6(1):229-234.

Bannon, et al., "Digestive Stability in the Context of Assessing the Potential Allergenicity of Food Proteins", Comments on Toxicology, vol. 8, 2002, 271-285.

Bateman, et al., "Identification of an Immunodominant Region of Fel d 1 and Characterization of Constituent Epitopes", Clinical & Experimental Allergy, vol. 38, Issue 11, Nov. 2008, pp. 1760-1768.

Bernard et al. "Allergenicity of peanut component Ara h 2: Contribution of conformational versus linear hydroxyproline-containing epitopes", J. Allergy Clin. Immunol. May 2015; 135(5):1267-74. e1-8. doi: 10.1016/j.iaci.2014.10.025. Epub Dec. 4, 2014.

Blanc, et al., "Capacity of Purified Peanut Allergens to Induce Degranulation in a Functional in Vitro Assay: Ara h 2 and Ara h 6 are the Most Efficient Elicitors", Clinical & Experimental Allergy, Aug. 2009, 39(8):1277-1285.

Blumchen, et al., "Oral Peanut Immunotherapy in Children with Peanut Anaphylaxis", Journal of Allergy and Clinical Immunology, Jul. 2010, 126(1):83-91.

Blumenthal et al. "Definition of an Allergen", Allergens and Allergen Immunotherapy. Ed. R. Lockey, S. Bukantz and J. Bousquet. New York: Marcel Decker, 2004, 37-50.

Bock, et al., "Further Fatalities Caused by Anaphylactic Reactions to Food, 2001-2006", Journal of Allergy and Clinical Immunology, Apr. 2007, 119(4):1016-1018.

Boumiza, et al., "The Basophil Activation Test by Flow Cytometry: Recent Developments in Clinical Studies, Standardization and Emerging Perspectives", Clinical and Molecular Allergy, vol. 3, No. 9, Jun. 30, 2005, pp. 1-8.

Burks, A Wesley, "Peanut Allergy", The Lancet, 371(9623):1538-1546.

Burks, et al., "Mapping and Mutational Analysis of the IgE-Binding Epitopes on Ara h 1, a Legume Vicilin Protein and a Major Allergen in Peanut Hypersensitivity", European Journal of Biochemistry, vol. 245, Jan. 9, 1997, pp. 334-339.

Burks, et al., "Peanut Allergens", Allergy, Sep. 1998, 53(8):725-730.

Burks, et al., "Peanut Induced Anaphylactic Reactions", International Archives of Allergy and Immunology, 1992, 119:165-172.

Busse, et al., "Recurrent Peanut Allergy", New England Journal of Medicine, vol. 347, 2002, pp. 1535-1536.

Campbell, et al., "Peptide Immunotherapy in Allergic Asthma Generates IL-10-Dependent Immunological Tolerance Associated with Linked Epitope Suppression", The Journal of Experimental Medicine, vol. 206, No. 7, pp. 1535-1547.

Chiang, et al., "Serological and Clinical Characteristics of Children with Peanut Sensitization in an Asian Community", Pediatric Allergy and Immunology, Aug. 2009, 21(2pt2):e429-e438.

Chruszcz, et al., "Structural and Immunologic Characterization of Ara h 1, a Major Peanut Allergen", Journal of Biological Chemistry vol. 286, No. 45, Nov. 11, 2011, 39318-39327.

Clark, et al., "Successful Oral Tolerance Induction in Severe Peanut Allergy", Allergy, Aug. 2009, 64(8):1218-1220.

Clarke, et al., "Serological Characteristics of Peanut Allergy", Clinical & Experimental Allergy, Oct. 1998, 28(10):1251-1257.

Cong et al. "Characterisation of the IgE-binding immunodominant epitopes on Ara h 1," Food Agric. Immunol. 19:175-185, 2008.

De Jong, et al., "Identification and Partial Characterization of Multiple Major Allergens in Peanut Proteins", Clinical & Experimental Allergy, Jun. 1998, 28(6):743-751.

De Leon, et al., "Immunological Analysis of Allergenic Cross Reactivity Between Peanut and Tree Nuts", Clinical and Experimental Allergy, 2003, 33(9):1273-1280.

De Leon, et al., "The Peanut Allergy Epidemic: Allergen Molecular Characterisation and Prospects for Specific Therapy", Expert Reviews in Molecular Medicine. vol. 9, Issue 1, Jan. 2007, pp. 1-18.

(56) References Cited

OTHER PUBLICATIONS

Delong, et al., "Ara h 1-Reactive T Cells in Peanut Allergic Individuals", Journal of Allergy and Clinical Immunology, vol. 127, No. 5, May 2011, pp. 1211-1218.
Drew, et al., "Hypoallergenic Variants of the Major Latex Allergen Hev b 6.01 Retaining Human T Lymphocyte Reactivity", The Journal of Immunology, Nov. 2004, 173(9):5872-5879.
Eusebius, et al., "Oligoclonal Analysis of the Atopic T Cell Response to the Group 1 Allergen of Cynodon dactylon (Bermuda Grass) Pollen: Pre- and Post-Allergen-Specific Immunotherapy", International Archives of Allergy and Immunology, Mar. 2002, 127(3):234 244.
Fellrath, et al., "Allergen-Specific T-Cell Tolerance Induction with Allergen-Derived Long Synthetic Peptides: Results of a Phase I Trial", Journal of Allergy and Clinical Immunology, Apr. 2003, 111(4):854-861.
Fried-Hajek et al. "Identification of a highly promiscuous and an HLA allele-specific T-cell epitope in the birch major allergen Bet v 1:HLA restriction, epitope mapping and TCR sequence comparisions," Clin. Exp. Allergy 29:478-487, 1999.
Genbank, U.S., 1996, L34402, URL, http://www.ncbi.nlm.nih.gov/nuccore/L34402.
Geunwoong, N. et al. (2012) Oral Sessions. Oral Abstract Session 1—"Allergen immunotherapy: new aspects in diagnostics and treatment." (Abstract 1, p. 1, "Tolerogenic effects of interferon-gamma with induction of allergen-specific interleukin-10 producing regulatory B cells (Br1) in non-IgE-mediated food allergy") Allergy (European Journal of Allergy and Clinical Immunology). 67, Suppl. 96 (2012):1-97.
Glaspole, et al., "Characterization of the T-cell Epitopes of a Major Peanut Allergen, ARA H 2", Allergy, 2005, 60:35-40.
Glaumann, et al., "Basophil Allergen Threshold Sensitivity, CD-sens, IgE-Sensitization and DBPCFC in Peanut-Sensitized Children", Allergy, Feb. 2012, 67(2):242-247.
Hall, et al., "Suppression of Allergen Reactive Th2 Mediated Responses and Pulmonary Eosinophilia by Intranasal Administration of an Immunodominant Peptide is Linked to IL-10 Production", Vaccine, 2003, 21(5-6):549-561.
Hemmer, et al., "Minimal Peptide Length Requirements for CD4+ T Cell Clones Implications for Molecular Mimicry and T Cell Survival", International Immunology, vol. 12, Issue 3, Mar. 1, 2000, pp. 375-383.
Zaunders, et al., "High Levels of Human Antigen-Specific CD4 T Cells in Peripheral Blood Revealed by Stimulated Coexpression of CD25 and CD134 (OX40)", The Journal of Immunology, 2009, 183:2827-2836.
Prickett et al., "Ara h 1 CD4+ T cell epitope-based peptides: candidates for a peanut allergy therapeutic", Journal of Clinical and Experimental Allergy. 2013;43:684-697.
Prickett, et al., "Ara h 2 Peptides Containing Dominant CD4(+) T-Cell Epitopes: Candidates for a Peanut Allergy Therapeutic", The Journal of Allergy and Clinical Immunology, Nov. 2010, 127(3):608-615.
Prickett, et al., "Immunoregulatory T cell epitope peptides: the new frontier in allergy therapy", Clinical & Experimental Allergy: Journal of the British Society for Allergy and Clinical Immunology, Jun. 16, 2015, 45(6):1015-1026.
Primeau, et al., "The Psychological Burden of Peanut Allergy as Perceived by Adults with Peanut Allergy and the Parents of Peanut-Allergic Children", Clinical & Experimental Allergy, Aug. 2000, 30(8):1135-1143.
Pumphrey, Richard, "Anaphylaxis: Can We Tell Who is at Risk of a Fatal Reaction?", Current Opinion in Allergy & Clinical Immunology, 2004, 4(4):285-290.
Robinson, Douglas S., "Th-2 Cytokines in Allergic Disease", British Medical Bulletin, vol. 56, Issue 4, Jan. 1, 2000, pp. 956-968.
Rolland et al. "Chapter 12 Peanut Allergy Biomolecular Characterization for Development of a Peanut T-cell Epitope Peptide Therapy", Food Allergy Molecular and Clinical Practice. Ed. Andreas Lopata CRC Press 2017.
Rolland, et al., "Allergen-Related Approaches to Immunotherapy", Pharmacology & Therapeutics, Mar. 2009, 121:273-284.
Rolland, et al., "Functional Regulatory T Cells and Allergen Immunotherapy", Current Opinion in Allergy and Clinical Immunology, vol. 10, Issue 6, Dec. 2010, pp. 559-566.
Ruiter, et al., "Role of Human Leucocyte Antigen DQ in the Presentation of T Cell Epitopes in the Major Cow's Milk Allergen alphas1-Casein", International Archives of Allergy and Immunology, vol. 143, No. 2, 2007, pp. 119-126.
Rupa, et al., "Oral Immunotherapy with Immunodominant T-Cell Epitope Peptides Alleviates Allergic Reactions in a Balb/c Mouse Model of Egg Allergy", Allergy, Jan. 2012, 67(1):74-82.
Sabatos-Peyton, et al., "Antigen-Specific Immunotherapy of Autoimmune and Allergic Diseases", Current Opinion in Immunology, vol. 22, No. 5, Oct. 2010, pp. 609-615.
Sampson, et al., "Fatal and Near-Fatal Anaphylactic Reactions to Food in Children and Adolescents", The New England Journal of Medicine, vol. 327, No. 6, Aug. 6, 1992, pp. 380-384.
Sampson, et al., "Risk-Taking and Coping Strategies of Adolescents and Young Adults with Food Allergy", Journal of Allergy and Clinical Immunology, vol. 117, Issue 6, Jun. 2006, pp. 1440-1445.
Santambrogio, et al., "Abundant Empty Class II MHC Molecules on the Surface of Immature Dendritic Cells", PNAS, Dec. 21, 1999, 96(26):15050-15055.
Schein, et al., "Bioinformatics Approaches to Classifying Allergens and Predicting Cross-Reactivity", Immunol Allergy Clin North Am. vol. 27, No. 1, Feb. 2007, 1-27.
Schultz, et al., "Expression and Secretion in Yeast of a 400-kda Envelope Glycoprotein Derived from Epstein-Barr Virus", Gene, 1987, 54(1): 113-123.
Shek, et al., "A Population-Based Questionnaire Survey on the Prevalence of Peanut, Tree Nut, and Shellfish Allergy in 2 Asian Populations", Journal of Allergy and Clinical Immunology, vol. 126, Issue 2, Aug. 2010, pp. 324-331.
Shreffler, et al., "Lack of Association of HLA Class II Alleles with Peanut Allergy", Annals of Allergy, Asthma & Immunology, vol. 96, Issue 6, Jun. 2006, pp. 865-869.
Shreffler, et al., "Microarray Immunoassay: Association of Clinical History, in Vitro IgE Function, and Heterogeneity of Allergenic Peanut Epitopes", Journal of Allergy and Clinical Immunology, vol. 113, Issue 4, Apr. 2004, pp. 776-782.
Sicherer, et al., "Clinical Features of Acute Allergic Reactions to Peanut and Tree Nuts in Children", Pediatrics, Jul. 1998, 102(1):1-6.
Sicherer, et al., "Prevalence of Peanut and Tree Nut Allergy in the US Determined by a Random Digit Dial Telephone Survey", Journal of Allergy and Clinical Immunology, vol. 103, No. 4, Apr. 1999, pp. 559-562.
Sicherer, et al., "US Prevalence of Self-Reported Peanut, Tree Nut, and Sesame Allergy: 11-Year Follow-Up", Journal of Allergy and Clinical Immunology, vol. 125, Issue 6, Jun. 2010, pp. 1322-1326.
Singh, et al., "ProPred: Prediction of HLA-DR Binding Sites", Bioinformatics, vol. 17, Issue 12, Dec. 1, 2001, pp. 1236-1237.
Skolnick et al. "From genes to protein structure and function: novel applications of computational approaches in the genomic era", Trends in Biotech. 18:34-39, 2000.
Srivastava, et al., "Immunotherapy with Modified Peanut Allergens in a Murine Model of Peanut Allergy", The Journal of Allergy and Clinical Immunology, Jan. 2002, 109(1):S287. Abstract.
Starkl, "An unfolded variant of the major peanut allergen Ara h 2 with decreased anaphylactic potential", Clinical & Experimental Allergy, Clinical & Experimental Allergy: Journal of the British Society for Allergy and Clinical Immunology, Dec. 6, 2012, 42(12):1801-1812.
Suri, et al., "The Wide Diversity and Complexity of Peptides Bound to Class II MHC Molecules", Current Opinion in Immunology, vol. 18, No. 1, Mar. 2006, pp. 70-77.
Tarzi, et al., "Induction of Interleukin-10 and Suppressor of Cytokine Signalling-3 Gene Expression Following Peptide Immunotherapy", Clinical & Experimental Allergy, Apr. 2006, 36(4):465-474.
Thyagarajan, et al., "Peanut Oral Immunotherapy is not ready for Clinical Use", Journal of Allergy and Clinical Immunology, Jul. 2010, 126(1):31-32.

(56) References Cited

OTHER PUBLICATIONS

Van Boxtel, "Determination of Pepsin-Susceptible and Pepsin-Resistant Epitopes in Native and Heat-Treated Peanut Allergen Ara h 1", Journal of Agricultural and Food Chemistry, vol. 56, No. 6, Mar. 26, 2008, pp. 2223-2230.
Van De Veen et al. (2012) "Oral Abstract Session 5—Abstract 26: Allergen-specific memory B-cell subsets in immune tolerance to allergens", Allergy. 67(Suppl. 96):1-97 (p. 12).
Van De Veen, et al., "Oral Abstract Session 6: Abstract 25", Allergy, 2012, 67 (Suppl 96), 1-97, p. 12.
Van Hoeyveld et al. "Allergenic and antigenic activity of peptide fragments in a whey hydrolysate formula", Clin. Exp. Allergy. Sep. 1998;28(9):1131-7.
Van Neerven, et al., "Characterization of Cat Dander-Specific T Lymphocytes from Atopic Patients", Journal of Immunology, vol. 152, No. 8, Apr. 15, 1994, pp. 4203-4210.
Varney, et al., "Usefulness of Immunotherapy in Patients with Severe Summer Hay Fever Uncontrolled by Antiallergic Drugs", British Medical Journal, Feb. 1, 1991, 302(6771):265-269.
Varshney, et al., "A Randomized Controlled Study of Peanut Oral Immunotherapy (OIT): Clinical Desensitization and Modulation of the Allergic", Journal of Allergy and Clinical Immunology, Mar. 2011, 127(3):654-660.
Varshney, et al., "Adverse Reactions During Peanut Oral Immunotherapy Home Dosing", Journal of Allergy and Clinical Immunology, Dec. 2009, 124(6):1351-1352.
Verhoef, et al., "Clonal Analysis of the Atopic Immune Response to the Group 2 Allergen of Dermatophagoides spp.: Identification of HLA-DR and -DQ Restricted T Cell Epitopes", International Immunology, vol. 5, No. 12, Jan. 1994, pp. 1589-1597.
Verhoef, et al., "T Cell Epitope Immunotherapy Induces a CD4+ T Cell Population with Regulatory Activity", PLoS Medicie, vol. 2, Issue 3, e78, Mar. 2005, 9 pages.
Vita, et al., "The Immune Epitope Database (IEDB) 3.0", Nucleic Acids Research, vol. 43, Database issue, 2015, pp. 405-412.
Vita, et al., "The Immune Epitope Database 2.0", Nucleic Acids Research, vol. 38, Issue suppl_1, Jan. 2010, pp. 854-862.
Worm, et al., "Cat Peptide Antigen Desensitisation for Treating Cat Allergic Rhinoconjunctivitis", Expert Opinion on Investigational Drugs, 2013, 22(10):1347-1357.
Worm, et al., "Development and Preliminary Clinical Evaluation of a Peptide Immunotherapy Vaccine for Cat Allergy", Journal of Allergy and Clinical Immunology, Jan. 2011, 127(1):89-97.
Yang, et al., "Multiple T Cell Epitope Peptides Suppress Allergic Responses in an Egg Allergy Mouse Model by the Elicitation of Forkhead Box Transcription Factor 3- and Transforming Growth Factor-Beta-Associated Mechanisms", Clinical & Experimental Allergy, Apr. 2010, 40(4):668-678.
Yoshitomi, et al., "Intraoral Administration of a T-Cell Epitope Peptide Induces Immunological Tolerance in Cry j 2-Sensitized Mice", Journal of Peptide Science, Aug. 2007, 13(8):499-503.
Yu, et al., "The Safety of Peanut Oral Immunotherapy in Peanut-Allergic Subjects in a Single-Center Trial", International Archives of Allergy and Immunology, Sep. 2012, 159(2):179-182.
Yun, et al., "Food Allergy in Adolescents and Adults", Internal Medicine Journal, vol. 39, No. 7, May 2009, pp. 475-478.
Higgins, et al., "Overlapping T-Cell Epitopes in the Group I allergen of Dermatophagoides Species Restricted by HLA-DP and HLA-DR Class II Molecules", Journal of Allergy Clinical Immunology, vol. 93, No. 5, 1994, pp. 891-899.
Hofmann, et al., "Safety of a Peanut Oral Immunotherapy Protocol in Children with Peanut Allergy", Journal of Allergy and Clinical Immunology, Aug. 2009, 124(2):286 291.
Hourihane, et al., "An Evaluation of the Sensitivity of Subjects with Peanut Allergy to Very Low Doses of Peanut Protein: A Randomized, Double-Blind, Placebo-Controlled Food Challenge Study", Journal of Allergy and Clinical Immunology, Nov. 1997, 100(5):596-600.
Hoyne, et al., "Inhibition of T Cell and Antibody Responses to House Dust Mite Allergen by Inhalation of the Dominant T Cell Epitope in Naive and Sensitized Mice", The Journal of Experimental Medicine, Nov. 1993, 178(5):1783-1788.
Husain, et al., "Peanut Allergy: An Increasingly Common Life-Threatening Disorder", Journal of the American Academy of Dermatology, Jan. 2012, 66(1):136-143.
Jameel, et al., "Hepatitis B Virus X Protein Produced in *Escherichia coli* Is Biologically Functional", Journal of Virology, Aug. 1990, 64(8):3963-3966.
Jones, et al., "Clinical Efficacy and Immune Regulation with Peanut Oral Immunotherapy", Journal of Allergy and Clinical Immunology, Aug. 2009, 124(2):292-300.
Kammerer, et al., "Modulation of T-Cell Response to Phospholipase A2 and Phospholipase A2-Derived Peptides by Conventional Bee Venom Immunotherapy", Journal of Allergy and Clinical Immunology, vol. 100, No. 1, 1997, pp. 96-103.
Kane, et al., "Cross-Linking of IgE-Receptor Complexes by Rigid Bivalent Antigens >200 Å in Length Triggers Cellular Degranulation", Journal of Biological Chemistry 1988, 969-980.
Kay, et al., "Allergen Immunotherapy with Cat Allergen Peptides", Springer Seminars in Immunopathology, vol. 25, Issue 3-4, Mar. 2004, pp. 391-399.
Kemp, et al., "Food Allergy and Anaphylaxis. Dealing with Uncertainty", The Medical Journal of Australia. May 2008, 188(9):503-504.
King, et al., "Allergenic Characteristics of Modified Peanut Allergen", Molecular Nutrition & Food Research, 2005, 49:963-971.
Kinnunen, et al., "Potential of an Altered Peptide Ligand of Lipocalin Allergen Bos d 2 for Peptide Immunotherapy", J. Allergy Clin. Immunol., Vo. 119, 2007, 965-972.
Kleber-Janke, et al., "Selective Cloning of Peanut Allergens, Including Profilin and 2S Albumins, by Phage Display Technology", International Archives of Allergy and Immunology, Aug. 1999, 119(4):265-274.
Knapp et al. (Mar. 1990) "pSEM Vectors: High Level Expression of Antigenic Determinants and Protein Domains", BioTechniques, 8(3):280-281.
Koppelman, "Relevance of Ara h1, Ara h2 and Ara h3 in Peanut Allergic Patients, as Determined by Immunoglobulin E Western Blotting, Basophil Histamine Release and Intracutaneous Testing: Ara h2 is the Most Important Peanut Allergen", Clinical & Experimental Allergy, Apr. 2004, 34(4):583-590.
Koppelman, et al., "Quantification of Major Peanut Allergens Ara h 1 and Ara h 2 in the Peanut Varieties Runner, Spanish, Virginia, and Valencia, Bred in Different Parts of the World", Allergy, Feb. 2001, 56(2):132-137.
Kurjan, et al., "Structure of a Yeast Pheromone Gene (MFalpha): A Putative alpha-Factor Precursor Contains Four Tandem Copies of Mature alpha-Factor", Cell, Oct. 1982, 30(3):933-943.
Kurucz et al. "Current Animal Models of Bronchial Asthma," Curr. Pharm. Des. 12:3175-3194, 2006.
Ladics, et al., "Bioinformatics and the Allergy Assessment of Agricultural Biotechnology Products: Industry Practices and Recommendations", Regulatory Toxicology and Pharmacology, vol. 60, 2011, 46-53.
Larché, Mark. "Mechanisms of Peptide Immunotherapy in Allergic Airways Disease", Transatlantic Airway Conference, vol. 11, Supp. 5, Dec. 2014, S292-296.
Larché, M, "Of Cats and Men: Immunodominance and the Role of HLA-DP/DQ", Clinical & Experimental Allergy, 38(11):1709-1711.
Lin, et al., "Patterns of Sensitization to Peanut Allergen Components in Taiwanese Preschool Children", Journal of Microbiology, Immunology and Infection, Apr. 2012, 45(2):90-95.
Litwin, et al., "Regulation of the Immune Response to Allergens by Immunosuppressive Allergenic Fragments", International Archives of Allergy and Immunology, 1988, 87(4):361-366.
Maguire, et al., "The Safety and Efficacy of Allervax Cat in Cat Allergic Patients", Clinical Immunology, vol. 93, Issue 3, Jan. 2000, pp. 222-231.
Mannering, et al., "An Efficient Method for Cloning Human Autoantigen-Specific T Cells", Journal of Immunological Methods, Mar. 2005, 298(1-2):83-92.

(56) References Cited

OTHER PUBLICATIONS

Marazuela, et al., "Intranasal Immunization with a Dominant T-Cell Epitope Peptide of a Major Allergen of Olive Pollen Prevents Mice from Sensitization to the Whole Allergen", Molecular Immunology, Jan. 2008, 45(2):438-445.

Marcotte, et al., "Effects of Peptide Therapy on Ex Vivo T-Cell Responses", Journal of Allergy and Clinical Immunology, Apr. 1998, 101(4):506-513.

Middleton, et al., "New Allele Frequency Database", Tissue Antigens, vol. 61, Issue 5, May 2003, pp. 403-407.

Mittag, et al., "The Effector T Cell Response to Ryegrass Pollen Is Counterregulated by Simultaneous Induction of Regulatory T Cells", The Journal of Immunology, Mar. 2010, 184:4708-4716.

Moldaver, et al., "Immunotherapy with Peptides", Allergy, Jun. 2011, 66(6):784-791.

Movérare, et al., "Evaluation of IgE Antibodies to Recombinant Peanut Allergens in Patients with Reported Reactions to Peanut", International Archives of Allergy and Immunology, Jun. 29, 2011, 156(3):282-290.

Mukherjee et al. "Allergic Astham: Influence of Genetic and Environmental Factors", J. Biol. Chem. 286(38):32883-32889, 2011.

Muller, et al., "Successful Immunotherapy with T-Cell Epitope Peptides of Bee Venom Phospholipase A2 Induces Specific T-cell Anergy in Patients Allergic to Bee Venom", Journal of Allergy and Clinical Immunology, Jun. 1998, 101(6):747-754.

Nelson, et al., "Treatment of Anaphylactic Sensitivity to Peanuts by Immunotherapy with Injections of Aqueous Peanut Extract", Journal of Allergy and Clinical Immunology, Jun. 1997, 99(6):744-751.

Ngo et al. "Computational Complexity, Protein Structure Prediction, and the Levinthal Paradox." The Protein Folding Problem and Tertiary Structure Prediction. Ed. K. Merz and S. Le Grand. Boston: Birkhauser, 1994, 491-495.

Nopp, et al., "Basophil Allergen Threshold Sensitivity: A Useful Approach to Anti-Ige Treatment Efficacy Evaluation", Allergy, Mar. 2006, 61(3)298-302.

Norman, et al., "Treatment of Cat Allergy with T-Cell Reactive Peptides", American Journal of Respiratory and Critical Care Medicine, Dec. 1, 1996, 154(6):1623-1628.

O'Hehir, et al., "House Dust Mite Sublingual Immunotherapy: The Role for Transforming Growth Factor-Beta and Functional Regulatory T Cells", American Journal of Respiratory and Critical Care Medicine, Nov. 15, 2009, 180(10):936-947.

O'Hehir, et al., "T Cell Epitope Peptide Therapy for Allergic Diseases", Current Allergy and Asthma Reports: Current Science, Jan. 14, 2016, 16(2):1-9.

Oldfield, et al., "Effect of T-Cell Peptides Derived from Fel d 1 on Allergic Reactions and Cytokine Production in Patients Sensitive to Cats: a Randomised Controlled Trial", The Lancet, Jul. 6, 2002, 360(9326):47-53.

Oppenheimer, et al., "Treatment of Peanut Allergy with Rush Immunotherapy", Journal of Allergy and Clinical Immunology, Aug. 1992, 90(2):256-262.

Otsu et al. (2014), "Epitope Analysis of Ara H2 and Ara H6: Characteristic Patterns of Ige-Binding Fingerprints Among Individuals with Similar Clinical Histories", Clinical & Experimental Allergy. 45(2):471-484.

Palmer, et al., "Comparative Potency of Ara h 1 and Ara h 2 in Immunochemical and Functional Assays of Allergenicity", Clinical Immunology, Jun. 2005, 115(3):302-312.

Palmer, et al., "Current Developments in Peanut Allergy", Current Opinion in Allergy and Clinical Immunology, vol. 6, No. 3, Jul. 2006, pp. 202-206.

Pascal, et al., "In Silico Prediction of Ara H 2 T Cell Epitopes in Peanut-Allergic Children", Clinical & Experimental Allergy, Jan. 2013, 43:116-127.

Peeters, et al., "Does Skin Prick Test Reactivity to Purified Allergens Correlate with Clinical Severity of Peanut Allergy?", Clinical & Experimental Allergy, Jan. 2007, 37(1):108-115.

Pene, et al., "Immunotherapy with Fel d 1 Peptides Decreases IL-4 Release by Peripheral Blood T Cells of Patients Allergic to Cats", Journal of Allergy and Clinical Immunology, Oct. 1998, 102(4):571-578.

Pomés, et al., "Quantification of Ara h 1 in Peanuts: Why Roasting Makes a Difference", Clinical & Experimental Allergy, Jun. 2006, 36(6):824-830.

Prickett et al. (2012) "Oral Abstract Session 5—Abstract 25: CD4+ T-cell epitope peptides with MHC-restriction diversity: candidates for a peanut allergy therapeutic," Allergy. 67(Suppl. 96):1-97 (p. 12).

FIG. 6

| Subject | No Antigen* | CPE | Stimulation Indices (SI) — Ara h 1 20-mers | | | | | | | | | +ve 20-mers | |
|---|---|---|---|---|---|---|---|---|---|---|---|---|---|
| | | | 23 | 24 | 40 | 46 | 47 | 49 | 50 | 51 | 57 | No. | % |
| 19 | 0.22 | 91.6 | 3.5 | 0.7 | 3.3 | nt | nt | nt | 0.7 | 3.2 | 36.0 | 4/6 | 67 |
| 20 | 0.08 | 1.4 | 1.1 | 1.4 | 0.0 | nt | nt | nt | 1.0 | 69.3 | 0.0 | 3/6 | 50 |
| 21 | 0.45 | 7.0 | 0.4 | 2.8 | 0.5 | nt | nt | nt | 0.3 | 1.0 | 0.4 | 1/6 | 17 |
| 22 | 0.27 | 54.6 | 0.4 | 0.9 | 0.2 | nt | nt | nt | 1.7 | 0.5 | 0.2 | 1/6 | 17 |
| 23 | 3.02 | 5.9 | 0.6 | 0.8 | 1.0 | nt | nt | nt | 1.2 | 0.4 | 2.0 | 2/6 | 33 |
| 24 | 0.26 | 6.8 | 0.5 | 0.5 | 0.6 | nt | nt | nt | 2.8 | 2.0 | 0.7 | 2/6 | 33 |
| 25 | 0.10 | 152.0 | 2.2 | 1.2 | 0.6 | 23.4 | 1.9 | 3.1 | 0.9 | 0.4 | 0.7 | 5/9 | 56 |
| 26 | 0.07 | 122.8 | 2.3 | 5.8 | 0.9 | 0.6 | 1.3 | 12.7 | 4.2 | 4.4 | 2.7 | 7/9 | 78 |
| 27 | 0.17 | 1.4 | 0.6 | 0.8 | 0.9 | 1.0 | 0.7 | 1.3 | 0.6 | 1.1 | 1.5 | 3/9 | 33 |
| 28 | 0.06 | 37.5 | 5.6 | 8.9 | 6.0 | 18.0 | 1.7 | 2.5 | 3.0 | 12.6 | 29.5 | 9/9 | 100 |
| 29 | 1.87 | 2.9 | 1.7 | 1.7 | 1.3 | 0.7 | 1.1 | 1.8 | 1.6 | 1.7 | 1.8 | 8/9 | 89 |
| 30 | 0.12 | 1.9 | 1.6 | 2.2 | 1.4 | 0.7 | 1.0 | 0.9 | 0.3 | 2.0 | 0.5 | 4/9 | 44 |
| 31 | 0.11 | 8.1 | 1.3 | 2.1 | 0.7 | 1.5 | 27.9 | 2.1 | 2.0 | 1.7 | 2.0 | 8/9 | 89 |
| 32 | 0.06 | 5.6 | 0.7 | 2.3 | 1.1 | 1.1 | 1.6 | 2.3 | 10.5 | 1.6 | 1.3 | 8/9 | 89 |
| 33 | 1.10 | 2.5 | 1.8 | 0.4 | 0.8 | 1.3 | 1.1 | 1.1 | 1.1 | 0.2 | 0.3 | 7/9 | 78 |
| 34 | 1.36 | 1.3 | 2.6 | 1.1 | 0.2 | 1.8 | 1.5 | 0.7 | 3.1 | 0.3 | 2.1 | 6/9 | 67 |
| 35 | 1.14 | 1.4 | 0.5 | 2.3 | 0.3 | 0.4 | 5.4 | 0.9 | 0.4 | 0.2 | 0.8 | 2/9 | 22 |
| 36 | 3.42 | 2.6^ | 0.8 | 0.3 | 1.2 | 1.6 | 1.3 | 0.5 | 0.1 | 0.3 | 0.2 | 3/9 | 33 |
| 37 | 0.38 | 5.5^ | 1.4 | 1.3 | 1.6 | 1.2 | 4.2 | 2.2 | 0.4 | 1.1 | 1.2 | 8/9 | 89 |
| 38 | 1.05 | 7.8 | 0.3 | 0.3 | 0.3 | 0.6 | 0.2 | 0.9 | 0.7 | 0.9 | 0.3 | 0/9 | 0 |
| 39 | 0.78 | 1.3 | 0.8 | 0.9 | 0.8 | 0.7 | 0.9 | 0.9 | 0.7 | 0.7 | 0.8 | 0/9 | 0 |
| Responder # | | 21/21 | 11/21 | 12/21 | 8/21 | 8/15 | 11/15 | 9/15 | 10/21 | 11/21 | 11/21 | | |
| Responder % | | 100 | 52 | 57 | 38 | 53 | 52 | 60 | 48 | 52 | 52 | | |
| 1 | 0.17 | 7.1 | 1.7 | 2.5 | 0.4 | 2.3 | 2.0 | 0.9 | 1.6 | 0.4 | 2.7 | 6/9 | 67 |
| 2 | 0.19 | 83.5 | 1.8 | 10.3 | 1.6 | 1.8 | 1.0 | 1.6 | 3.4 | 1.9 | 2.9 | 8/9 | 89 |
| 4 | 0.62 | 12.3 | 5.2 | 1.8 | 4.2 | nt | nt | nt | 4.7 | 6.5 | 9.7 | 6/6 | 100 |
| 10 | 0.23 | 44.4 | 14.4 | 5.3 | 5.3 | nt | nt | nt | 14.2 | 8.1 | 4.4 | 6/6 | 100 |

FIG. 7

| 20-mer peptide # Residues | Minimum T-cell stimulatory sequence Residues | Sequence | Consolidated epitope (common core underlined) Residues/aa | Sequence | Confirmed Responders TCL | Sub-jects |
|---|---|---|---|---|---|---|
| 23 (199-218) | (206-213) | FQNLQNHR | | | | |
| | (206-215) | FQNLQNHRIV | (206-215) 10 aa | FQNLQNHRIV | 6 | 3 |
| 24 (208-227) | (213-222) | RIVQIEAKPN | | | | |
| | (213-225) | RIVQIEAKPNTLV | (213-225) 13 aa | RIVQIEAKPNTLV | 6 | 3 |
| | (214-219) | IVQIEA | | | | |
| | Overlapping epitopes combined | | (206-225) 20 aa | FQNLQNHRIVQIEAKPNTLV* | 12 | 6 |
| 40 (352-371) | (353-371) | WSTRSSENNEGVIVKVSKE | | | | |
| | (359-371) | ENNEGVIVKVSKE | (353-371) 19 aa | WSTRSSENNEGVIVKVSKE* | 3 | 3 |
| | (361-370) | NEGVIVKVSK | | | | |
| 46 (406-425) | (409-418) | NNFGKLFEVK | | | | |
| | (409-425) | NNFGKLFEVKPDKKNPQ | (409-425) 17 aa | NNFGKLFEVKPDKKNPQ | 3 | 2 |
| | (411-418) | FGKLFEVK | | | | |
| 47 (415-434) | (416-427) | EVKPDKKNPQLQ | (416-427) 12 aa | EVKPDKKNPQLQ | 2 | 1 |
| | Overlapping epitopes combined | | (409-427) 19 aa | NNFGKLFEVKPDKKNPQLQ* | 3 | 2 |
| 49 (433-452) | (436-445) | VEIKEGALML | | | | |
| | (436-449) | VEIKEGALMLPHFN | (436-452) 17 aa | VEIKEGALMLPHFNSKA* | 5 | 2 |
| | (440-452) | EGALMLPHFNSKA | | | | |
| 50 (443-461) | (442-458) | ALMLPHFNSKAMVIVVV | | | | |
| | (443-457) | LMLPHFNSKAMVIVV | (442-458) 17 aa | ALMLPHFNSKAMVIVVV* | 6 | 3 |
| | (446-456) | PHFNSKAMVIV | | | | |
| | (451-459) | KAMVIVVVN | | | | |
| | (452-461) | AMVIVVVNKG | (451-461) 11 aa | KAMVIVVVNKG | 3 | 2 |
| | (453-461) | MVIVVVNKG | | | | |
| 51 (451-470) | (452-467) | AMVIVVVNKGTGNLEL | | | | |
| | (452-468) | AMVIVVVNKGTGNLELV | | | | |
| | (453-469) | VVNKGTGNLELVA | (452-470) 19 aa | AMVIVVVNKGTGNLELVAV | 7 | 4 |
| | (457-470) | VVNKGTGNLELVAV | | | | |
| | Overlapping epitopes combined | | (451-470) 20 aa | KAMVIVVVNKGTGNLELVAV* | 10 | 6 |
| 57 (505-524) | (507-524) | GDVFIMPAAHPVAINASS | | | | |
| | (509-524) | VFIMPAAHPVAINASS | | | | |
| | (510-521) | FIMPAAHPVAIN | (507-524) 18 aa | GDVFIMPAAHPVAINASS* | 12 | 4 |
| | (511-517) | IMPAAHP | | | | |
| | (511-521) | IMPAAHPVAIN | | | | |

FIG. 8

| 20-mer | Epitope | Subject | HLA-restriction | Corresponding HLA-allele(s) | |
|---|---|---|---|---|---|
| 23 | (206-215) | 18 | HLA-DR | DRB1 04:05 | DRB1 15:01 |
|  |  | 3 | HLA-DR | DRB1 03:01 | DRB1 08:01 |
| 24 | (213-225) | 12 | HLA-DR | DRB1 08:01 | DRB1 10:01 |
|  |  | 10 | HLA-DR | DRB1 11:01 | DRB1 15:01 |
| 40 | (353-371) | 4 | HLA-DQ | DQB1 03:01 | DQB1 06:02 |
|  |  | 13 | HLA-DQ | DQB1 03:01 | DQB1 06:02 |
|  |  | 14 | nt | DQB1 06:09 |  |
| 46 | (409-425) | 16 | HLA-DR | DRB1 04:04 | DRB1 13:01 |
|  |  | 15 | ND | DRB1 03:01P | DRB1 04:01 |
| 47 | (416-427) | 16 | HLA-DR | DRB1 04:04 | DRB1 13:01 |
|  |  | 15 | nt | DRB1 03:01P | DRB1 04:01 |
| 49 | (436-452) | 18 | HLA-DQ | DQB1 03:02 | DQB1 06:02 |
|  |  |  | HLA-DR | DRB1 04:05 | DRB1 15:01 |
| 50 | (442-458) | 17 | HLA-DR | DRB1 11:04 | DRB1 15:01 |
|  |  | 9 | HLA-DR | DRB1 09:01 | DRB1 13:01 |
| 50+51 | (451-461) | 12 | HLA-DR | DRB1 08:01 | DRB1 10:01 |
|  |  | 6 | HLA-DR | DRB1 04:01 | DRB1 04:04 |
| 51 | (452-470) | 10 | HLA-DR | DRB1 11:01 | DRB1 15:01 |
|  |  | 14 | nt | DRB1 13:02 |  |
| 57 | (507-524) | 17 | HLA-DR | DRB1 11:04 | DRB1 15:01 |
|  |  | 13 | HLA-DQ | DQB1 03:01 | DQB1 06:02 |

Ara h 1 20-mer peptide

| HLA molecule | 23 (199-218) | 24 (208-227) | 46 (406-425) | 47 (415-434) | 49 (433-452) | 50 (442-461) | 51 (451-470) | 57 (505-524) |
|---|---|---|---|---|---|---|---|---|
| DRB1_1323 | FDQRSRQFQNLQNHRIVQIEE | NLQNHRIVQIEEAKPNTLVLP | DLSNNFGKLFEVKPDKKNPQ | FEVKPDKKNPQLQDLDMMLT | LTCVEIKEGALMLPHFNSKA | ALMLPHFNSKAMVIVVNKG | KAMVIVVNKGTGNLELVAV | KEGDVFIMPAAHPVAINASS |
| DRB1_1327 | FDQRSRQFQNLQNHRIVQIEE | NLQNHRIVQIEEAKPNTLVLP | DLSNNFGKLFEVKPDKKNPQ | FEVKPDKKNPQLQDLDMMLT | LTCVEIKEGALMLPHFNSKA | ALMLPHFNSKAMVIVVNKG | KAMVIVVNKGTGNLELVAV | KEGDVFIMPAAHPVAINASS |
| DRB1_1328 | FDQRSRQFQNLQNHRIVQIEE | NLQNHRIVQIEEAKPNTLVLP | DLSNNFGKLFEVKPDKKNPQ | FEVKPDKKNPQLQDLDMMLT | LTCVEIKEGALMLPHFNSKA | ALMLPHFNSKAMVIVVNKG | KAMVIVVNKGTGNLELVAV | KEGDVFIMPAAHPVAINASS |
| DRB1_1501 | FDQRSRQFQNLQNHRIVQIEE | NLQNHRIVQIEEAKPNTLVLP | DLSNNFGKLFEVKPDKKNPQ | FEVKPDKKNPQLQDLDMMLT | LTCVEIKEGALMLPHFNSKA | ALMLPHFNSKAMVIVVNKG | KAMVIVVNKGTGNLELVAV | KEGDVFIMPAAHPVAINASS |
| DRB1_1502 | FDQRSRQFQNLQNHRIVQIEE | NLQNHRIVQIEEAKPNTLVLP | DLSNNFGKLFEVKPDKKNPQ | FEVKPDKKNPQLQDLDMMLT | LTCVEIKEGALMLPHFNSKA | ALMLPHFNSKAMVIVVNKG | KAMVIVVNKGTGNLELVAV | KEGDVFIMPAAHPVAINASS |
| DRB1_1506 | FDQRSRQFQNLQNHRIVQIEE | NLQNHRIVQIEEAKPNTLVLP | DLSNNFGKLFEVKPDKKNPQ | FEVKPDKKNPQLQDLDMMLT | LTCVEIKEGALMLPHFNSKA | ALMLPHFNSKAMVIVVNKG | KAMVIVVNKGTGNLELVAV | KEGDVFIMPAAHPVAINASS |
| DRB5_0101 | FDQRSRQFQNLQNHRIVQIEE | NLQNHRIVQIEEAKPNTLVLP | DLSNNFGKLFEVKPDKKNPQ | FEVKPDKKNPQLQDLDMMLT | LTCVEIKEGALMLPHFNSKA | ALMLPHFNSKAMVIVVNKG | KAMVIVVNKGTGNLELVAV | KEGDVFIMPAAHPVAINASS |
| DRB5_0105 | FDQRSRQFQNLQNHRIVQIEE | NLQNHRIVQIEEAKPNTLVLP | DLSNNFGKLFEVKPDKKNPQ | FEVKPDKKNPQLQDLDMMLT | LTCVEIKEGALMLPHFNSKA | ALMLPHFNSKAMVIVVNKG | KAMVIVVNKGTGNLELVAV | KEGDVFIMPAAHPVAINASS |

FIG. 11

| Sub-ject | No Antigen* | CPE | Stimulation Indices (SI) Candidate peptides | | | | | | | +ve peptides | |
|---|---|---|---|---|---|---|---|---|---|---|---|
| | | | 206-225 | 353-371 | 409-427 | 436-452 | 442-458 | 451-470 | 507-524 | No. | % |
| 1 | 0.17 | 7.1^ | 2.4 | 2.7 | 1.8 | 5.5 | 1.8 | 1.1 | 1.7 | 7/7 | 100 |
| 30 | 0.12 | 1.9 | 1.2 | 0.5 | 1.6 | 6.2 | 0.3 | 0.8 | 0.8 | 3/7 | 43 |
| 31 | 0.11 | 8.1 | 1.3 | 2.9 | 0.7 | 5.4 | 1.6 | 1.5 | 27.9 | 6/7 | 86 |
| 32 | 0.06 | 5.6 | 0.7 | 2.4 | 1.1 | 0.9 | 0.7 | 1.1 | 1.6 | 4/7 | 57 |
| 33 | 1.10 | 2.5 | 0.7 | 0.7 | 1.4 | 0.6 | 0.5 | 0.6 | 0.7 | 1/7 | 14 |
| 34 | 1.36 | 1.3^ | 1.7 | 0.8 | 2.1 | 1.6 | 2.3 | 1.9 | 1.7 | 6/7 | 86 |
| 35 | 1.14 | 1.4^ | 0.3 | 0.4 | 0.3 | 0.3 | 0.5 | 2.6 | 0.8 | 1/7 | 14 |
| 36 | 3.42 | 2.6^ | 0.4 | 0.5 | 1.0 | 1.7 | 0.4 | 0.1 | 1.6 | 2/7 | 28 |
| 37 | 0.38 | 5.5^ | 1.8 | 1.2 | 2.2 | 3.8 | 2.0 | 0.3 | 2.0 | 6/7 | 86 |
| Responder No. | | 9/9 | 5/9 | 4/9 | 6/9 | 6/9 | 4/9 | 5/9 | 6/9 | | |
| Responder % | | 100 | 56 | 44 | 67 | 67 | 44 | 56 | 67 | | |

IMMUNOTHERAPEUTIC MOLECULES AND USES THEREOF

RELATED APPLICATIONS

This application is a continuation application of U.S. patent application Ser. No. 14/440,025, filed on Apr. 30, 2015, which is a U.S. national stage application, filed under 35 U.S.C. § 371, of International Application No. PCT/AU2013/001255, filed Oct. 30, 2013, which claims the benefit of Australian Patent Application No. 2012904780, filed Oct. 30, 2012, the contents of each of which are incorporated herein by reference in their entireties.

INCORPORATION BY REFERENCE

The contents of the text file named "28616-501N01US_ST25.txt," which was created on Aug. 3, 2015 and is 13 KB in size, are hereby incorporated by reference in their entirety.

FIELD OF THE INVENTION

The present invention relates generally to molecules such as peptides, polypeptides and proteins which interact immunologically with T lymphocytes in subjects having peanut allergy, or allergy to other tree nuts, and genetic sequences encoding same. These molecules are preferably immunointeractive with T cells in subjects having an allergy to the Ara h 1 allergen. The molecules of the present invention are useful in the development of diagnostic, therapeutic and prophylactic agents for conditions characterised by an aberrant, inappropriate or otherwise unwanted immune response to Ara h 1 or derivative or homologue thereof.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Peanut allergy is a life-threatening and incurable disorder, affecting approximately 1% of the general population (Husain et al. *J Am Acad Dermatol.* 66(1):136-43, 2012, Burks, *Lancet.* 371(9623):1538-46, 2008). It is characterised by the sudden onset of anaphylaxis, which may occur with exposure to minute quantities of peanut proteins (Hourihane et al., *J Allergy Clin Immunol* 100: 596-600, 1997; Pumphrey, *Current Opinion in Allergy & Clinical Immunology.* 4(4): 285-90, 2004). Nut induced anaphylaxis is that most frequently associated with mortality or with life-threatening features (Bock et al. *J Allergy Clin Immunol.* 119(4):1016-8, 2007; Burks 2008, supra). Peanut proteins are frequently concealed within apparently safe food sources, such that accidental contact occurs for up to 50% of sufferers over a 5 year period (Sicherer et al., *Paediatrics* 102: e6, 1998). Not surprisingly, nut allergy is associated with significant psychological morbidity for sufferers and carers alike, akin to that suffered by those with chronic debilitating illnesses such as rheumatoid arthritis (Primeau et al., *Clin Exp Allergy* 30: 1135-43, 2000; Kemp et al. *Med. J. Aust.* 188(9):503-4, 2008). Cure, while being an imperative to remove nut allergy as a cause of mortality, is also necessary to remove the chronic psychological burden that peanut allergic subjects carry.

To date, efforts at immunotherapy for peanut allergy have been met by extremely limited success. Nelson et al. have shown that tolerance of peanut can be induced using a rush immunotherapy protocol, but that tolerance is lost in approximately half of the subjects during maintenance dosing and additionally that injections are associated with frequent episodes of anaphylaxis in the majority of subjects during both the buildup and maintenance phases (Nelson et al., *J Allergy Clin Immunol* 99: 744-51, 1997). Oppenheimer et al. demonstrated similar findings within their study, again showing that active therapy is associated with a high rate of systemic anaphylaxis. Data collection in that study was terminated after the administration of peanut extract to a placebo randomised subject resulted in their death, highlighting the dangerous nature of this condition (Oppenheimer et al., *J Allergy Clin Immunol* 90: 256-62, 1992). Recent studies of oral immunotherapy with whole peanut flour provide encouragement that desensitization is feasible, but the observed adverse reactions highlight major safety concerns (Hofmann et al. *J. Allergy Clin. Immunol.* 124, 286, 2009; Jones et al. *J. Allergy Clin. Immunol.* 24, 292, 2009; Clark et al. *Allergy* 64, 1218, 2009; Varshney et al. *J Allergy Clin Immunol.* 127(3):654-60, 2011; Varshney et al. *J Allergy Clin Immunol.* 124(6):1351-2, 2009; Anagnostou et al. *Clin Exp Allergy.* 41(9):1273-81, 2011; Allen & O'Hehir. *Clin Exp Allergy.* 41(9):1172-4, 2011; Yu et al. *Int Arch Allergy Immunol.* 159(2):179-182, 2012; Thyagarajan et al. *J Allergy Clin Immunol.* 126(1):31-2, 2010; Blumchen et al. *J Allergy Clin Immunol.* 126(1):83-91, 2010). Even with the exclusion of children prone to severe symptoms or asthma, two studies reported an anaphylactic episode, in one case during an initial food challenge (Clark et al. *Allergy* 64, 1218, 2009) and in the other during treatment of a child who had not previously experienced anaphylaxis (Hofmann et al. *J. Allergy Clin. Immunol.* 124, 286, 2009).

Development of novel strategies to overcome the morbidity associated with allergen immunotherapy depends on an accurate understanding of the immunological basis to successful immunotherapy, as well as its side-effects. It has long been established that morbidity due to allergen immunotherapy is due to the cross-linking of IgE, and that this action is not required for such therapy to be efficacious (Litwin et al., *Int Arch Allergy Appl Immunol* 87: 361-61, 998). It is also known that one of the critical actions of immunotherapy in producing tolerance is its ability to change the predominant specific T cell phenotype from a $T_H2$ to a regulatory phenotype. These regulatory T cells act via production of the anti-inflammatory cytokines IL-10 and/or TGFβ. (Akdis & Akdis, *J Allergy Clin Immunol.* 123:735-46, 2009; Akdis & Akdis, *Nature Reviews: Drug Discovery.* 8:645-60. 2009; Akdis & Akdis, *J Allergy Clin Immunol.* 127:18-27, 2011).

A key difference in antibody and lymphocyte responses is in antigen recognition, antibodies recognising conformational epitopes dependent on molecular tertiary structure, while CD4+ T cells recognise short linear peptides. This difference in antigen recognition is the basis to many novel strategies of immunotherapy, including that using peptides based upon T cell epitopes, B cell epitope mutants and altered peptide ligands (Rolland et al. *Pharmacology & Therapeutics* 121:273-284, 2009). Such methods all depend on the alteration or absence molecular tertiary structure, so that IgE cross-linking and effector cell activation is lost. Peptide immunotherapy is a method in respect of which evidence of efficacy exists, being documented for both cat dander allergy and bee venom allergy. Three different studies showed that, in the absence of any systemic side-effects, tolerance could be achieved for the major bee venom allergen Phospholipase A2 (PLA2) using T cell epitope-containing sequences (Muller et al. *J Allergy Clin Immunol.* 101: 747-54, 1998; Tarzi et al. *Clin Exp Allergy.* 36: 465-74, 2006; Fellrath et al. *J Allergy Clin Immunol.* 111: 854-61, 2003), while several studies have demonstrated that peptides based on the structure of the major cat allergen Fel d 1 can be used to induce diminished clinical responses (Norman et al., *Am J Respir Crit Care Med* 154: 1623-8, 1996; Marcotte et al., *J Allergy Clin Immunol* 101: 506-13, 1998; Pene et al., *J Allergy Clin Immunol* 102: 571-8, 1998; Oldfield et al. *Lancet* 360:47-53, 2002; Alexander et al. *Clin Exp Allergy* 35: 52-8, 2004; Alexander et al. *Allergy* 60:1269-74, 2005). Most recently, a phase IIa trial confirmed the safety, tolerability and potential efficacy of a seven-peptide mixture from Fel d 1 (Toleromune Cat©, Cicassia Ltd., Oxford, UK) (Worm et al. *J Allergy Clin Immunol.* 127: 89-97, 2011) with Phase IIb trials now underway (Moldaver & Larche. *Allergy.* 66: 784-91, 2011). Crucial to the development of such strategies is the retention of T cell epitopes, so that T cell phenotypic change can be induced.

The ability to bind directly on to MHC class II molecules allows peptides to be presented by non-professional or immature APC without pro-inflammatory and co-stimulatory signals which promotes induction of tolerance, anergy and/or suppressive activity in responding T cells (Moldaver & Larche, *Allergy* 66: 784-91, 2011). This also allows peptides to be presented at higher frequency than peptides processed from the whole molecule (Santambrogio et al. *Proc Natl Acad Sci USA,* 1999, 96:15056-61), and since they are also safer than whole allergen, peptides can be given at higher concentrations, thus repolarising T cell responses more effectively.

Importantly, targeting T cells specific for dominant epitopes of major allergens can alter responses to whole allergen extracts (linked suppression). Many studies reporting successful peptide immunotherapy in murine models of allergy demonstrated that administration of dominant T-cell epitope peptides of major allergens induced tolerance not only to those peptides, but also to purified allergen and whole allergen extracts (Yang et al. *Clin Exp Allergy* 40(4): 668-78, 2010; Yoshitomi et al. *J Pept Sci.* 13(8):499-503, 2007; Marazuela et al. *Mol Immunol.* 45(2):438-45, 2008; Rupa et al. *Allergy.* 67(1):74-82, 2012; Hoyne et al. *J Exp Med.* 178(5):1783-8, 1993; Hall et al. *Vaccine.* 21(5-6):549-61, 2003).

Accordingly, there is a need to both identify the major peanut allergens and, further, to identify the T cell epitopes of these allergens. The identification characterisation, and analysis of these epitopes is critical to the development of specific diagnostic and immunotherapeutic methodology. To this end, although the Ara h 1 peanut allergen molecule has previously been the subject of analysis, the identification of the T cell core epitopic regions, which are essential to the development of an effective vaccine, has not been achieved. Still further, previous studies have been limited by the fact that they have been based on the use of HLA-DR tetramers thereby preventing detection of epitopes presented by other HLA types. Since the effectiveness of a vaccine across the general population necessitates that the epitopes in issue can be presented across a range of different HLA types, there is a need not only to identify the T cell epitopes within the Ara h 1 molecule but, further, to identify the epitopes which are both dominant and can be effectively presented by the diverse HLA types which are representative of the population.

In work leading up to the present invention, dominant, HLA-degenerate Ara h 1 core epitopic regions have been identified. This group of core epitopic regions is unique in terms of its particularly high level of efficacy. Unlike the previously studied 20mer Ara h 1 peptides which were identified based only on their ability to exhibit some level of T cell reactivity, the sequences of the present invention are a selected set of core T cell epitope regions which are both immunodominant, relative to other Ara h 1 peptide fragments, and are also HLA degenerate in that they bind to two or more HLA types. Still further, these epitopic core regions are presented by HLA-DQ molecules. HLA-DQ molecules are more conserved in mixed populations than HLA-DR molecules. Accordingly, peptides presented on HLA-DQ enable broader population coverage. The identification of this specific group of core epitopic regions has facilitated, for the first time, the development of effective methods for the treatment of conditions characterised by aberrant, inappropriate or otherwise unwanted immune responses to Ara h 1 or derivative or homologue thereof, other tree-nut allergy or allergy to a composition, such as foods containing the Ara h 1 allergen. The identification of these epitopes has also facilitated the development of corresponding diagnostic technology.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains amino acid sequence information prepared using the programme Patent In Version 3.5, presented herein after the bibliography. Each amino acid sequence is identified in the sequence listing by the numeric indicator <210> followed by the sequence identifier (eg. <210>1, <210>2, etc). The length, type of sequence (protein, etc) and source organism for each sequence is indicated by information provided in the numeric indicator fields <211>, <212> and <213>, respectively. Amino acid sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

One aspect of the present invention is directed to a composition comprising one or more Ara h 1 T cell core epitopic regions selected from the list consisting of:

(i)
    (SEQ ID NO: 1)
FQNLQNHR
(ii)
    (SEQ ID NO: 2)
IVQIEA
(iii)
    (SEQ ID NO: 3)
NEGVIVKVSK
(iv)
    (SEQ ID NO: 4)
FGKLFEVK
(v)
    (SEQ ID NO: 5)
EVKPDKKNPQLQ
(vi)
    (SEQ ID NO: 6)
EGALML
(vii)
    (SEQ ID NO: 7)
PHFNSKAMVIV
(viii)
    (SEQ ID NO: 8)
IVVVN
(ix)
    (SEQ ID NO: 9)
VVNKGTGNLEL
(x)
    (SEQ ID NO: 10)
IMPAAHP or functional derivatives or homologues thereof.

In a related aspect the present invention is directed to a composition comprising one or more peptides, each of which peptides is up to 60 contiguous amino acids in length and which peptides include one or more Ara h 1 T cell core epitopic regions selected from the list consisting of:

(i)
    (SEQ ID NO: 1)
FQNLQNHR
(ii)
    (SEQ ID NO: 2)
IVQIEA
(iii)
    (SEQ ID NO: 3)
NEGVIVKVSK
(iv)
    (SEQ ID NO: 4)
FGKLFEVK
(v)
    (SEQ ID NO: 5)
EVKPDKKNPQLQ
(vi)
    (SEQ ID NO: 6)
EGALML
(vii)
    (SEQ ID NO: 7)
PHFNSKAMVIV
(viii)
    (SEQ ID NO: 8)
IVVVN
(ix)
    (SEQ ID NO: 9)
VVNKGTGNLEL
(x)
    (SEQ ID NO: 10)
IMPAAHP or functional derivatives or homologues thereof.

In one embodiment of the preceding aspects of the invention, said peptides or epitopes are capable of modifying T cell function when presented to T cells isolated from subjects having a condition characterised by an aberrant, unwanted or otherwise inappropriate immune response to Ara h 1 but which peptides are unable to bind to Ara h 1-specific IgE.

In a further related aspect there is provided a composition comprising one or more peptides, each of which peptide is up to 60 contiguous amino acids in length and which peptides include one or more Ara h 1 T cell core epitopic regions selected from the list consisting of:

(i)
    (SEQ ID NO: 1)
FQNLQNHR
(ii)
    (SEQ ID NO: 2)
IVQIEA
(iii)
    (SEQ ID NO: 3)
NEGVIVKVSK
(iv)
    (SEQ ID NO: 4)
FGKLFEVK
(v)
    (SEQ ID NO: 5)
EVKPDKKNPQLQ
(vi)
    (SEQ ID NO: 6)
EGALML
(vii)
    (SEQ ID NO: 7)
PHFNSKAMVIV
(viii)
    (SEQ ID NO: 8)
IVVVN
(ix)
    (SEQ ID NO: 9)
VVNKGTGNLEL
(x)
    (SEQ ID NO: 10)
IMPAAHP or functional derivatives or homologues thereof, which peptides are capable of reducing Ara h 1 hypersensitivity or hypersensitivity to a composition comprising Ara h 1 when administered to a subject having a condition characterised by said hypersensitivity.

In another aspect there is provided a composition comprising one or more peptides, each of which peptides is up to 60 contiguous amino acids in length and which peptides include the epitope NEGVIVKVSK (SEQ ID NO:3) together with one or more Ara h 1 T cell core epitopic regions selected from the list consisting of:

(i)
    (SEQ ID NO: 1)
FQNLQNHR
(ii)
    (SEQ ID NO: 2)
IVQIEA
(iii)
    (SEQ ID NO: 4)
FGKLFEVK
(iv)
    (SEQ ID NO: 5)
EVKPDKKNPQLQ
(v)
    (SEQ ID NO: 6)
EGALML
(vi)
    (SEQ ID NO: 7)
PHFNSKAMVIV
(vii)
    (SEQ ID NO: 8)
IVVVN

```
            -continued
(viii)
                    (SEQ ID NO: 9)
VVNKGTGNLEL
(ix)
                    (SEQ ID NO: 10)
IMPAAHP
``` or functional derivatives or homologues thereof.

In still another aspect there is provided a composition comprising one or more peptides, each of which peptides is up to 60 contiguous amino acids in length and which peptide includes epitope EGALML (SEQ ID NO:6) together with one or more Ara h 1 T cell core epitopic regions selected from the list consisting of:

```
(i)
                    (SEQ ID NO: 1)
FQNLQNHR
(ii)
                    (SEQ ID NO: 2)
IVQIEA
(iii)
                    (SEQ ID NO: 3)
NEGVIVKVSK
(iv)
                    (SEQ ID NO: 4)
FGKLFEVK
(v)
                    (SEQ ID NO: 5)
EVKPDKKNPQLQ
(vi)
                    (SEQ ID NO: 7)
PHFNSKAMVIV
(vii)
                    (SEQ ID NO: 8)
IVVVN
(viii)
                    (SEQ ID NO: 9)
VVNKGTGNLEL
(ix)
                    (SEQ ID NO: 10)
IMPAAHP
``` or functional derivatives or homologues thereof.

To the extent that the composition is designed such that the core epitopic regions of the invention are included as part of a larger peptide, it should be understood that any given peptide may be designed to include one or more core epitopic regions. To this end, in one embodiment of the present invention, the one or more peptides of the subject composition are selected from the list:

```
(i)
                    (SEQ ID NO: 12)
FQNLQNHRIV
(ii)
                    (SEQ ID NO: 13)
RIVQIEAKPNTLV
(iii)
                    (SEQ ID NO: 14)
FQNLQNHRIVQIEAKPNTLV
(iv)
                    (SEQ ID NO: 15)
WSTRSSENNEGVIVKVSKE
(v)
                    (SEQ ID NO: 16)
STRSSENNEGVIVKVSKE
(vi)
                    (SEQ ID NO: 17)
ENNEGVIVKVSKE
(vii)
                    (SEQ ID NO: 18)
NNFGKLFEVKPDKKNPQ
```

```
            -continued
(viii)
                    (SEQ ID NO: 19)
SNNFGKLFEVKPDKKNPQ
(ix)
                    (SEQ ID NO: 20)
EVKPDKKNPQLQ
(x)
                    (SEQ ID NO: 21)
NNFGKLFEVKPDKKNPQLQ
(xi)
                    (SEQ ID NO: 22)
SNNFGKLFEVKPDKKNPQLQ
(xii)
                    (SEQ ID NO: 23)
VEIKEGALMLPHFNSKA
(xiii)
                    (SEQ ID NO: 24)
ALMLPHFNSKAMVIVVV
(xiv)
                    (SEQ ID NO: 25)
KAMVIVVVNKG
(xv)
                    (SEQ ID NO: 26)
AMVIVVVNKGTGNLELVAV
(xvi)
                    (SEQ ID NO: 27)
VVNKGTGNLELVAVRK
(xvii)
                    (SEQ ID NO: 28)
AMVIVVVNKGTGNLELV
(xviii)
                    (SEQ ID NO: 29)
KAMVIVVVNKGTGNLELVAV
(xix)
                    (SEQ ID NO: 30)
GDVFIMPAAHPVAINASS
(xx)
                    (SEQ ID NO: 31)
VFIMPAAHPVAINASSE
(xxi)
                    (SEQ ID NO: 32)
GDVFIMPAAHPVAINASSE
(xxii)
                    (SEQ ID NO: 33)
VFIMPAAHPVAINASS
```

In a further aspect of this embodiment, said composition comprises the peptide defined by SEQ ID NO:15, 16 or 17 together with one or more of the peptides defined by SEQ ID NOs:12-14 or 18-33.

In still a further aspect of this embodiment, said composition comprises the peptide defined by SEQ ID NO:23 together with one or more of the peptides defined by SEQ ID NOs:12-22 or 24-33.

BRIEF DESCRIPTION OF THE DRAWINGS

FIG. 6 is a table showing CFSE-based detection of peanut-allergic donor CD4+ T-cell proliferation in response to selected Ara h 1 20-mers. Upper panel shows new peanut-allergic donor cohort; lower panel shows four subjects from peanut-allergic donor cohort used for TCL generation. CPE, crude peanut extract; +ve, positive; nt, not tested (peptide stocks not available at time of testing); Grey, stimulation indices >1.1<2.5; Black, stimulation indices >2.5
*Background proliferation with no antigen, % CD4+CFSE$^{lo}$ T cells of total CD4+ T cells; ^A combination of enriched Ara h 1 and Ara h 1 (10 μg/mL of each) was used instead of CPE for these subjects.

FIG. 7 is a table showing core T-cell epitope sequences mapped within selected Ara h 1 20-mers. Grey shading indicates overlapping consolidated epitope pairs combined into single peptides for further analyses. *The seven candidate peptides proposed for a therapeutic.

FIG. 8 is a table showing HLA class II restriction of core epitope peptides. nt=not tested (TCL not available); Grey shading indicates overlapping epitope pairs combined into single peptides for further analyses.

FIG. 10 is a table showing predicted HLA-DR binding motifs in selected Ara h 1 20-mers. HLA-DR binding motifs (grey shading) were predicted using the ProPred algorithm (http:www.immuneepitope.org; accessed 30 Jan. 2012). Predicted primary anchor residues are bolded and underlined. Peptide 40 (352-371 is not shown as no HLA-DR binding motifs were predicted for this peptide by this algorithm.

FIG. 11 is a table showing CFSE-based detection of peanut-allergic donor CD4+ T-cell proliferation in response to selected Ara h 1 candidate peptides. CPE, crude peanut extract; +ve, positive; Grey, stimulation indices >1.1<2.5; Black, stimulation indices >2.5
*Background proliferation with no antigen, % CD4+CFSE$^{lo}$ T cells of total CD4+ T cells ^A combination of enriched Ara h 1 and Ara h 1 (10 μg/mL of each) was used instead of CPE for these subjects.

DETAILED DESCRIPTION OF THE INVENTION

Figure 1:
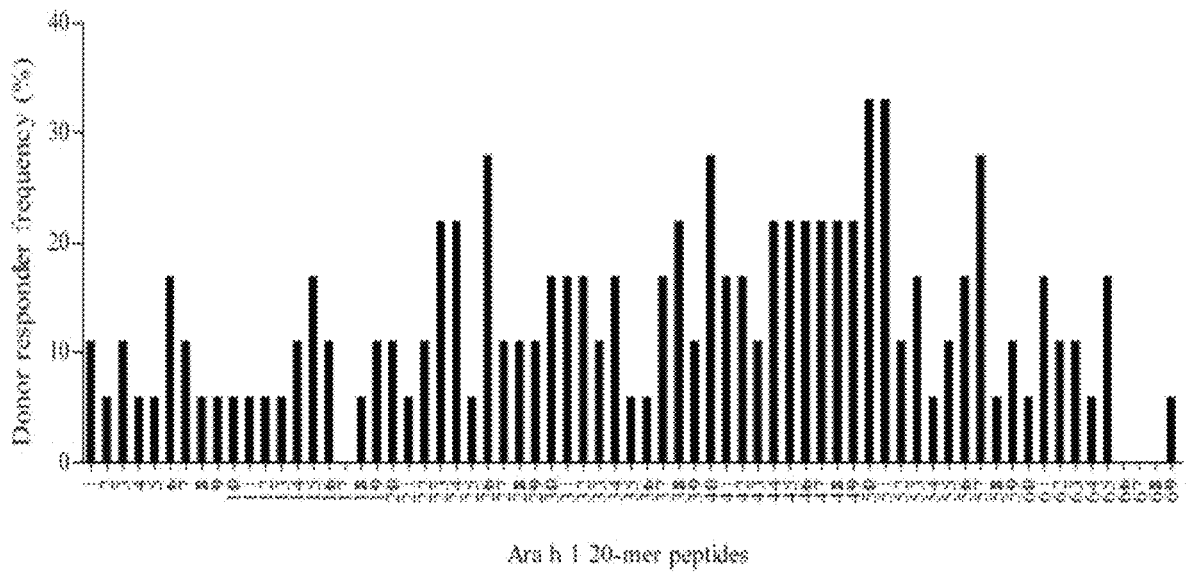
FIG. 1: Donor responder frequency profile for Ara h 1 20-mer peptides Donor responder frequencies for TCL recognition of Ara h 1 20-mer peptides (n=18 peanut-allergic subjects).

The present invention is predicated, in part, on the identification of HLA degenerate Ara h 1 dominant T cell core epitopic regions. The identification of these immunodominant core epitopic regions has enabled improvement of diagnostic methodology and the development of significantly more efficacious therapeutic and prophylactic compositions and treatment approaches, than have been available to date, for conditions such as, but not limited to, peanut allergy.

Accordingly, one aspect of the present invention is directed to a composition comprising one or more Ara h 1 T cell core epitopic regions selected from the list consisting of:

(i)
                              (SEQ ID NO: 1)
FQNLQNHR
(ii)
                              (SEQ ID NO: 2)
IVQIEA
(iii)
                              (SEQ ID NO: 3)
NEGVIVKVSK
(iv)
                              (SEQ ID NO: 4)
FGKLFEVK
(v)
                              (SEQ ID NO: 5)
EVKPDKKNPQLQ
(vi)
                              (SEQ ID NO: 6)
EGALML
(vii)
                              (SEQ ID NO: 7)
PHFNSKAMVIV
(viii)
                              (SEQ ID NO: 8)
IVVVN
(ix)
                              (SEQ ID NO: 9)
VVNKGTGNLEL
(x)
                              (SEQ ID NO: 10)
IMPAAHP or functional derivatives or homologues thereof.

In a related aspect the present invention is directed to a composition comprising one or more peptides, each of which peptides is up to 60 contiguous amino acids in length and which peptides include one or more Ara h 1 T cell core epitopic regions selected from the list consisting of:

(i)
                              (SEQ ID NO: 1)
FQNLQNHR
(ii)
                              (SEQ ID NO: 2)
IVQIEA
(iii)
                              (SEQ ID NO: 3)
NEGVIVKVSK
(iv)
                              (SEQ ID NO: 4)
FGKLFEVK
(v)
                              (SEQ ID NO: 5)
EVKPDKKNPQLQ
(vi)
                              (SEQ ID NO: 6)
EGALML -continued (vii)
```
                    (SEQ ID NO: 7)
PHFNSKAMVIV
```
(viii)
```
                    (SEQ ID NO: 8)
IVVVN
```
(ix)
```
                    (SEQ ID NO: 9)
VVNKGTGNLEL
```
(x)
```
                    (SEQ ID NO: 10)
IMPAAHP
``` or functional derivatives or homologues thereof.

In one embodiment of the preceding aspects of the invention, said peptides or core epitopic regions are capable of modifying T cell function when presented to T cells isolated from subjects having a condition characterised by an aberrant, unwanted or otherwise inappropriate immune response to Ara h 1 or to an allergen present in a composition, such as food, comprising Ara h 1 but which peptides are unable to bind to Ara h 1-specific IgE.

Without limiting the present invention in any way, peanuts contain many proteins, with the number of distinct bands visible on SDS-PAGE depending on the methodology used. Up to 53 bands are visible following high pressure liquid chromatography (de Jong et al., *Clin Exp Allergy* 28: 743-51, 1998). Only two of these proteins warrant classification as major allergens using standard criteria, whereby IgE reactivity occurs within greater than 50% of the peanut allergic population; these proteins are termed Ara h 1 and Ara h 2 (Burks et al., *Allergy* 53: 725-30, 1998). Although a number of studies have indicated Ara h 2 to be the more potent of these two allergens (Blanc et al. *Clin Exp Allergy.* 2009; 39(8):1277-85; Koppelman et al. *Clin Exp Allergy.* 2004; 34(4):583-90; Palmer et al. *Clin Immunol.* 2005; 115(3):302-12), Ara h 1 also plays a major role in the pathogenesis of peanut allergy, with numerous studies reporting strong correlations between symptom severity and IgE reactivity to both Ara h 1 and Ara h 2 (Glaumann et al. *Allergy.* 2012; 67(2):242-7; Chiang et al. *Pediatr Allergy Immunol.* 2009; 21(2 Pt 2):e429-38; Asarnoj et al. *Allergy.* 2010, 65(9):1189-95; Moverare et al. *Int Arch Allergy Immunol* 2011; 156(3):282-90; Lin et al. *J Microbiol Immunol Infect.* 2012; Peeters et al. *Clin Exp Allergy.* 2007; 37(1): 108-15). Ara h 1 is the most abundant major allergen in peanut, accounting for 12-16% of total peanut protein (Koppelman et al. *Allergy.* 2001; 56(2):132-7).

Still without limiting the present invention in any way, the Ara h 1 allergen is a 7S seed storage glycoprotein or vicilin. The concentration of Ara h 1 in peanuts increases with the size of the kernel (4-16 mg extracted Ara h 1/g peanut), so expression of the protein is associated with peanut maturity (Pomes et al. 2006, *Clin. Exp. Allergy* 36(6):824-30). Ara h 1 is a homotrimer held together through hydrophobic areas at the distal ends of the monomers, where most of the IgE binding epitopes are located. Each 64.5 kD monomer has a cupin motif which consists of two core ꞵ-barrels, each associated to a loop domain of α-helices.

Reference to "Ara h 1" should be understood as a reference to all forms of this molecule including reference to any isoforms which may arise from alternative splicing of Ara h 1 mRNA or functional mutant or polymorphic forms of Ara h 1. It should still further be understood to extend to any protein encoded by the Ara h 1 gene, any subunit polypeptide, such as precursor forms which may be generated, whether existing as a monomer, multimer or fusion protein. It also includes reference to analogues or equivalents of Ara h 1 such as may occur where a product which naturally comprises Ara h 1 is synthetically generated for the purpose of generating a product such as a food additive. The present invention thereby provides epitopes and methods for their use in the diagnosis and treatment of any condition characterised by hypersensitivity to an Ara h 1 or Ara h 1-like molecule, such as peanut allergy or a tree-nut allergy, or an allergy to an antigen present in a composition, such as food, which composition also comprises Ara h 1. Preferably, said Ara h 1 comprises the sequence set forth in SEQ ID NO:11.

Reference to "T cells" should be understood as a reference to any cell comprising a T cell receptor. In this regard, the T cell receptor may comprise any one or more of the α, β, y or δ chains. The present invention is not intended to be limited to any particular functional sub-class of T cells although in a preferred embodiment the subject T cell is a T helper cell and still more preferably a Th2-type cell and/or Treg cell. In this regard, reference to "modifying T cell function" should be understood as a reference to modifying any one or more functions which a T cell is capable of performing. For example, the subject function may be proliferation, differentiation or other form of cellular functional activity such as the production of cytokines. In one embodiment the subject functional activity is proliferation.

In terms of "modifying the function" of T cells isolated from subjects having a condition characterised by an aberrant, unwanted or inappropriate immune response to Ara h 1 or to a composition which comprises Ara h 1, it should be understood that this is not necessarily a reference to modifying the function of all the T cells in a given biological sample but is likely, in fact, to reflect the modification of functioning of only some of the T cells in the sample. For example, only a portion of the T helper cells in a given T cell sample may functionally respond to contact with the subject peptide. Such a partial response should be understood to fall within the scope of the present invention. It should also be understood that the T cells which are derived from the subject may be freshly harvested T cells or they may have undergone some form of in vitro or in vivo manipulation prior to testing. For example, T cell lines may have been generated from the cell sample and it is these T cell lines which then form the subject derived T cell population which is tested in accordance with the present invention. To the extent that the subject functional activity is T cell proliferation, the T cell proliferation assay is preferably performed as disclosed herein. Still more preferably, the subject modification of T cell function is the induction of proliferation. In this regard, reference to "Ara h 1-reactive" T cell should be understood as a reference to a T cell which responds functionally to HLA presentation of an Ara h 1 T cell epitope. Similarly, reference to "Ara h 1-specific" IgE should be understood as a reference to IgE directed to Ara h 1 B cell epitopes.

Reference to an "aberrant, unwanted or otherwise inappropriate" immune response should be understood as a reference to any form of physiological activity which involves the activation and/or functioning of one or more immune cells where that activity is inappropriate in that it is of an inappropriate type or proceeds to an inappropriate degree. It may be aberrant in that according to known immunological principals it either should not occur when it does so or else should occur when it does not do so. In another example, the immune response may be inappropriate in that it is a physiologically normal response but which is unnecessary and/or unwanted, such as occurs with respect to type-I hypersensitivity responses to innocuous allergens. In the context of the present invention, this immune response may be directed to Ara h 1 or it may be directed to a different allergen which is present in a composition together with Ara h 1. Without limiting the present invention to any one theory or mode of action, it has been determined that even where the hypersensitivity response is directed to an allergen other than Ara h 1, which allergen is present in a composition which nevertheless comprises Ara h 1, treatment via the method of the present invention which is directed to Ara h 1 nevertheless induces beneficial modulation of Th2 and Treg functionality such that the hypersensitivity which exists to the unrelated allergen is nevertheless reduced. Preferably said immune response is peanut hypersensitivity.

By "peanut hypersensitivity" is meant the induction of clinical symptoms of IgE mediated peanut hypersensitivity. However, it should be understood that although clinical symptoms may be evident, not all such individuals would necessarily exhibit detectable levels of peanut specific serum IgE which is measured using the Kallestad Allercoat EAST System (Sanofi-Pasteur Diagnostics, USA), although such individuals should nevertheless be understood to fall within the scope of the definition of those exhibiting "peanut hypersensitivity". Alternatively, testing may proceed utilising either the Pharmacia or the UniCap systems. Reference to "Ara h 1 hypersensitivity" should be understood to have a corresponding meaning in the context of reactivity to the Ara h 1 protein.

In a further related aspect there is provided a composition comprising one or more peptides, each of which peptide is up to 60 contiguous amino acids in length and which peptides include one or more Ara h 1 T cell core epitopic regions selected from the list consisting of:

```
         (i)
                    (SEQ ID NO: 1)
    FQNLQNHR
         (ii)
                    (SEQ ID NO: 2)
    IVQIEA
         (iii)
                    (SEQ ID NO: 3)
    NEGVIVKVSK
         (iv)
                    (SEQ ID NO: 4)
    FGKLFEVK
         (v)
                    (SEQ ID NO: 5)
    EVKPDKKNPQLQ
         (vi)
                    (SEQ ID NO: 6)
    EGALML
         (vii)
                    (SEQ ID NO: 7)
    PHFNSKAMVIV
         (viii)
                    (SEQ ID NO: 8)
    IVVVN
         (ix)
                    (SEQ ID NO: 9)
    VVNKGTGNLEL
         (x)
                    (SEQ ID NO: 10)
    IMPAAHP
``` or functional derivatives or homologues thereof, which peptides are capable of reducing Ara h 1 hypersensitivity or hypersensitivity to a composition comprising Ara h 1 when administered to a subject having a condition characterised by said hypersensitivity.

The reduction of Ara h 1 hypersensitivity (and allergen hypersensitivity more generally) is discussed in more detail hereafter. Briefly, however, this may take the form of either partially or completely desensitising or tolerising an individual to Ara h 1 specifically or peanut or other proteins more generally.

Reference to a "peptide" includes reference to a peptide, polypeptide or protein or parts thereof. The peptide may be glycosylated or unglycosylated and/or may contain a range of other molecules fused, linked, bound or otherwise associated to the protein such as amino acids, lipids, carbohydrates or other peptides, polypeptides or proteins. Reference hereinafter to a "peptide" includes a peptide comprising a sequence of amino acids as well as a peptide associated with other molecules such as amino acids, lipids, carbohydrates or other peptides, polypeptides or proteins.

"Derivatives" include fragments, parts, portions and variants from natural, synthetic or recombinant sources including fusion proteins. Parts or fragments include, for example, active regions of the subject peptide. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence.

Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins.

Chemical and functional equivalents of the subject peptide should be understood as molecules exhibiting any one or more of the functional activities of these molecules and may be derived from any source such as being chemically synthesized or identified via screening processes such as natural product screening.

Homologues include peptides derived from varieties other than peanuts, such as peptides derived from other tree nuts.

Analogues contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues. Mutants include molecules which exhibit modified functional activity (for example, Ara h 1 peptides which express one or more T cell epitopes but lack B cell reactivity).

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |

TABLE 1-continued

| Non-conventional amino acid | Code | Non-conventional amino acid | Code |
|---|---|---|---|
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

It is possible to modify the structure of a peptide according to the invention for various purposes such as for increasing solubility, enhancing therapeutic or preventative efficacy, enhancing stability or increasing resistance to proteolytic degradation. A modified peptide may be produced in which the amino acid sequence has been altered, such as by amino acid substitution, deletion or addition, to modify immunogenicity and/or reduce allergenicity. Similarly components may be added to peptides of the invention to produce the same result.

For example, a peptide can be modified so that it exhibits the ability to induce T cell anergy. In this instance, critical binding residues for the T cell receptor can be determined using known techniques (for example substitution of each residue and determination of the presence or absence of T cell reactivity) In one example, those residues shown to be essential to interact with the T cell receptor can be modified by replacing the essential amino acid with another, preferably similar amino acid residue (a conservative substitution) whose presence is shown to alter T cell reactivity or T cell functioning. In addition, those amino acid residues which are not essential for T cell receptor interaction can be modified by being replaced by another amino acid whose incorporation may then alter T cell reactivity or T cell functioning but does not, for example, eliminate binding to relevant MHC proteins. In yet another example, mutant peptides may be created which exhibit normal T cell binding but abrogated IgE binding.

Exemplary conservative substitutions are detailed in Table 2, below, and include:

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Such modifications will result in the production of molecules falling within the scope of "mutants" of the subject peptide as herein defined. "Mutants" should be understood as a reference to peptides which exhibit one or more structural features or functional activities which are distinct from those exhibited by the non-mutated peptide counterpart. Peptides of the invention may also be modified to incorporate one or more polymorphisms resulting from natural allelic variation and D-amino acids, non-natural amino acids or amino acid analogues may be substituted into the peptides to produce modified peptides which fall within the scope of the invention. Peptides may also be modified by conjugation with polyethylene glycol (PEG) by known techniques. Reporter groups may also be added to facilitate purification and potentially increase solubility of the peptides according to the invention. Other well known types of modification including insertion of specific endoprotease cleavage sites, addition of functional groups or replacement of hydrophobic residues with less hydrophobic residues as well as site-directed mutagenesis of DNA encoding the peptides of the invention may also be used to introduce modifications which could be useful for a wide range of purposes. The various modifications to peptides according to the invention which have been mentioned above are mentioned by way of example only and are merely intended to be indicative of the broad range of modifications which can be effected.

As detailed hereinbefore, the present invention provides peptides which retain all or some of their capacity to interact with T cells but exhibit partially or completely inhibited, abrogated or otherwise down-regulated antibody reactivity. Effecting the down-regulation of antibody reactivity can be achieved by any suitable method, which methods would be well known to those skilled in the art. For example, to the extent that a B cell epitope is defined by its linear amino acid sequence, one may add, delete or substitute one or more amino acid residues in order to render the mutated linear sequence distinct from the naturally occurring sequence. To the extent that an epitope may be additionally, or alternatively, defined by a conformational epitope, one may seek to disrupt that conformation by disrupting a 2° or, to the extent that homodimers or heterodimers exist, a 3° structure of the peptide. This may be achieved, for example, by disrupting the formation of bonds, such as disulphide bonds, which are known to stabilise 2° and/or 3° structures. In terms of the T cell epitopes hereinbefore defined, these epitopic regions do not comprise B cell epitopes.

The epitopes defined by SEQ ID NOs:1-10 are the T cell core epitopic regions of Ara h 1 which have been determined to also exhibit HLA degeneracy, in particular presentation by HLA-DQ, this being crucial in terms of developing an effective treatment regime. It should be understood that the composition of the present invention may comprise one of the listed core epitopic regions or it may comprise two or more of these core epitopic regions.

In one embodiment, said composition comprises any two epitopic regions, three epitopic regions, four epitopic regions, five epitopic regions, six epitopic regions, seven epitopic regions, eight epitopic regions, nine epitopic regions or ten epitopic regions.

In another embodiment there is provided a composition comprising one or more peptides, each of which peptides is up to 60 contiguous amino acids in length and which peptides include the epitope NEGVIVKVSK (SEQ ID NO:3) together with one or more Ara h 1 T cell core epitopic regions selected from the list consisting of:

(i)
                               (SEQ ID NO: 1)
FQNLQNHR
(ii)
                               (SEQ ID NO: 2)
IVQIEA
(iii)
                               (SEQ ID NO: 4)
FGKLFEVK
(iv)
                               (SEQ ID NO: 5)
EVKPDKKNPQLQ
(v)
                               (SEQ ID NO: 6)
EGALML
(vi)
                               (SEQ ID NO: 7)
PHFNSKAMVIV
(vii)
                               (SEQ ID NO: 8)
IVVVN
(viii)
                               (SEQ ID NO: 9)
VVNKGTGNLEL
(ix)
                               (SEQ ID NO: 10)
IMPAAHP or functional derivatives or homologues thereof.

In still another embodiment there is provided a composition comprising one or more peptides, each of which peptides is up to 60 contiguous amino acids in length and which peptide includes epitope EGALML (SEQ ID NO:6) together with one or more Ara h 1 T cell core epitopic regions selected from the list consisting of:

(i)
                               (SEQ ID NO: 1)
FQNLQNHR
(ii)
                               (SEQ ID NO: 2)
IVQIEA
(iii)
                               (SEQ ID NO: 3)
NEGVIVKVSK
(iv)
                               (SEQ ID NO: 4)
FGKLFEVK
(v)
                               (SEQ ID NO: 5)
EVKPDKKNPQLQ
(vi)
                               (SEQ ID NO: 7)
PHFNSKAMVIV
(vii)
                               (SEQ ID NO: 8)
IVVVN
(viii)
                               (SEQ ID NO: 9)
VVNKGTGNLEL
(ix)
                               (SEQ ID NO: 10)
IMPAAHP or functional derivatives or homologues thereof.

In accordance with these aspects, in other embodiments said composition includes at least three peptides, at least four peptides, at least five peptides, at least six peptides, at least seven peptides, at least eight peptides, at least nine peptides or ten peptides.

As detailed hereinbefore, the composition of the present invention comprises HLA degenerate, Ara h 1 T cell core epitopic regions. These core epitopic regions may be administered as stand alone peptides or they may form part of a larger structure, such as a longer peptide or a non-peptide structure. As would be appreciated by the person of skill in the art, an epitopic region can sometimes be too small, in its own right, to induce an immune response. Haptens are an example of this type of epitope. The core epitopic regions of the present invention may therefore be formulated together with any proteinaceous or non-proteinaceous carrier molecule, so as to achieve the necessary level of immunogenicity.

In one embodiment, the subject core epitopic regions form part of a larger peptide of up to 30 contiguous amino acids in length. The subject peptide may be 10, 11, 12, 13, 14, 15, 16, 17, 18, 19, 20, 21, 22, 23, 24, 25, 26, 27, 28, 29 or 30 amino acids in length. Preferably, the subject peptide is 12-25 amino acids in length, 15-25 amino acids in length, 15-20 amino acids in length, or 10-20 amino acids in length.

To the extent that the composition is designed such that the core epitopic regions of the invention are included as part of a larger peptide, it should be understood that any given peptide may be designed to include one or more core epitopic regions. To this end, in one embodiment of the present invention, the one or more peptides of the subject composition are selected from the list:

```
(i)
                        (SEQ ID NO: 12)
FQNLQNHRIV
(ii)
                        (SEQ ID NO: 13)
RIVQIEAKPNTLV
(iii)
                        (SEQ ID NO: 14)
FQNLQNHRIVQIEAKPNTLV
(iv)
                        (SEQ ID NO: 15)
WSTRSSENNEGVIVKVSKE
(v)
                        (SEQ ID NO: 16)
STRSSENNEGVIVKVSKE
(vi)
                        (SEQ ID NO: 17)
ENNEGVIVKVSKE
(vii)
                        (SEQ ID NO: 18)
NNFGKLFEVKPDKKNPQ
(viii)
                        (SEQ ID NO: 5)
EVKPDKKNPQLQ
(ix)
                        (SEQ ID NO: 19)
SNNFGKLFEVKPDKKNPQ
(x)
                        (SEQ ID NO: 21)
NNFGKLFEVKPDKKNPQLQ
(xi)
                        (SEQ ID NO: 22)
SNNFGKLFEVKPDKKNPQLQ
(xii)
                        (SEQ ID NO: 23)
VEIKEGALMLPHFNSKA
(xiii)
                        (SEQ ID NO: 24)
ALMLPHFNSKAMVIVVV
(xiv)
                        (SEQ ID NO: 25)
KAMVIVVVNKG
(xv)
                        (SEQ ID NO: 26)
AMVIVVVNKGTGNLELVAV
(xvi)
                        (SEQ ID NO: 27)
VVNKGTGNLELVAVRK
(xvii)
                        (SEQ ID NO: 28)
AMVIVVVNKGTGNLELV
(xviii)
                        (SEQ ID NO: 29)
KAMVIVVVNKGTGNLELVAV
(xix)
                        (SEQ ID NO: 30)
GDVFIMPAAHPVAINASS
```

```
-continued
(xx)
                        (SEQ ID NO: 31)
VFIMPAAHPVAINASSE
(xxi)
                        (SEQ ID NO: 32)
GDVFIMPAAHPVAINASSE
(xxii)
                        (SEQ ID NO: 33)
VFIMPAAHPVAINASS
```

In a further aspect of this embodiment, said composition comprises the peptide defined by SEQ ID NO:15, 16 or 17 together with one or more of the peptides defined by SEQ ID NOs:12-14 or 18-33.

In still a further aspect of this embodiment, said composition comprises the peptide defined by SEQ ID NO:23 together with one or more of the peptides defined by SEQ ID NOs:12-22 or 24-33.

In yet another aspect, the one or more peptides of the subject composition are selected from the list:

```
(i)
                        (SEQ ID NO: 12)
FQNLQNHRIV
(ii)
                        (SEQ ID NO: 13)
RIVQIEAKPNTLV
(iii)
                        (SEQ ID NO: 14)
FQNLQNHRIVQIEAKPNTLV
(iv)
                        (SEQ ID NO: 15)
WSTRSSENNEGVIVKVSKE
(v)
                        (SEQ ID NO: 16)
STRSSENNEGVIVKVSKE
(vi)
                        (SEQ ID NO: 18)
NNFGKLFEVKPDKKNPQ
(vii)
                        (SEQ ID NO: 19)
SNNFGKLFEVKPDKKNPQ
(viii)
                        (SEQ ID NO: 5)
EVKPDKKNPQLQ
(ix)
                        (SEQ ID NO: 21)
NNFGKLFEVKPDKKNPQLQ
(x)
                        (SEQ ID NO: 22)
SNNFGKLFEVKPDKKNPQLQ
(xi)
                        (SEQ ID NO: 23)
VEIKEGALMLPHFNSKA
(xii)
                        (SEQ ID NO: 24)
ALMLPHFNSKAMVIVVV
(xiii)
                        (SEQ ID NO: 25)
KAMVIVVVNKG
(xiv)
                        (SEQ ID NO: 26)
AMVIVVVNKGTGNLELVAV
(xv)
                        (SEQ ID NO: 28)
AMVIVVVNKGTGNLELV
(xvi)
                        (SEQ ID NO: 29)
KAMVIVVVNKGTGNLELVAV
(xvii)
                        (SEQ ID NO: 30)
GDVFIMPAAHPVAINASS
(xviii)
                        (SEQ ID NO: 32)
GDVFIMPAAHPVAINASSE
(xix)
                        (SEQ ID NO: 31)
VFIMPAAHPVAINASSE
```

In a further aspect of this embodiment, said composition comprises the peptide defined by SEQ ID NO:15 or 16 together with one or more of the peptides defined by SEQ ID NOs:12-14, 18-26 or 28-32.

In still a further aspect of this embodiment, said composition comprises the peptide defined by SEQ ID NO:23 together with one or more of the peptides defined by SEQ ID NOs:12-16, 18-22, 24-26 or 28-32.

In still yet another embodiment, said one or more peptides of the subject composition are selected from the list:

```
(i)
                        (SEQ ID NO: 14)
FQNLQNHRIVQIEAKPNTLV
(ii)
                        (SEQ ID NO: 15)
WSTRSSENNEGVIVKVSKE
(iii)
                        (SEQ ID NO: 21)
NNFGKLFEVKPDKKNPQLQ
(iv)
                        (SEQ ID NO: 23)
VEIKEGALMLPHFNSKA
(v)
                        (SEQ ID NO: 24)
ALMLPHFNSKAMVIVVV
(vi)
                        (SEQ ID NO: 29)
KAMVIVVVNKGTGNLELVAV
(vii)
                        (SEQ ID NO: 30)
GDVFIMPAAHPVAINASS.
```

In a further aspect of this embodiment, said composition comprises the peptide defined by SEQ ID NO:15 together with one or more of the peptides defined by SEQ ID NOs:14, 21, 23, 24, 29 or 30.

In still a further aspect of this embodiment, said composition comprises the peptide defined by SEQ ID NO:23 together with one or more of the peptides defined by SEQ ID NOs:14, 15, 21, 24, 29 or 30.

In still another embodiment, said composition comprises the peptides defined by SEQ ID NOs:14, 15, 21, 23, 24, 29 and 30.

In yet another embodiment, said composition comprises the peptides defined by SEQ ID NOs:14, 16, 21, 23, 24, 29 and 30.

In still yet another embodiment, said composition comprises the peptides defined by SEQ ID NOs:14, 15, 22, 23, 24, 29 and 30.

In yet still another embodiment, said composition comprises the peptides defined by SEQ ID NOs:14, 15, 21, 23, 24, 29 and 32.

In the context of the present invention, it should be understood that where reference is made to the use of the peptide defined by SEQ ID NO:14, this peptide may be substituted by:
(i) the peptides defined by SEQ ID NOs: 12 and 13;
(ii) the peptide defined by SEQ ID NO:12; or
(iii) the peptide defined by SEQ ID NO:13.

To the extent that reference is made to the use of the peptide defined by SEQ ID NO:15, this peptide may be substituted by the peptide defined by SEQ ID NO:16 or 17.

To the extent that reference is made to the use of the peptide defined by SEQ ID NO:21, this peptide may be substituted by the peptide defined by:
(i) the peptide defined by SEQ ID NO:22;
(ii) the peptides defined by SEQ ID NOs:18 and 20;
(iii) the peptides defined by SEQ ID NOs:20 and 19;
(iv) the peptide defined by SEQ ID NO:18;
(v) the peptide defined by SEQ ID NO:19; or
(vi) the peptide defined by SEQ ID NO:20.

To the extent that reference is made to the use of the peptide defined by SEQ ID NO:29, this peptide may be substituted by the peptide defined by:
(i) the peptides defined by SEQ ID NOs:25, 28 and 27;
(ii) the peptides defined by SEQ ID NOs:25 and 26;
(iii) the peptides defined by SEQ ID NOs:25 and 28;
(iv) the peptides defined by SEQ ID NOs:25 and 27;
(v) the peptides defined by SEQ ID NO:25;
(vi) the peptide defined by SEQ ID NO:28;
(vii) the peptide defined by SEQ ID NO:27; or
(viii) the peptide defined by SEQ ID NO:26.

To the extent that reference is made to the use of the peptide defined by SEQ ID NO:30, this peptide may be substituted by the peptide defined by:
(i) the peptide defined by SEQ ID NO:32;
(ii) the peptide defined by SEQ ID NO:33; or
(iii) the peptide defined by SEQ ID NO:31.

In a still further aspect of these embodiments, said composition comprises 3 or 4 or 5 or 6 of the listed peptides.

In still another embodiment, said composition comprises all 7 peptides.

The peptides of the present invention may be prepared by recombinant or chemical synthetic means. According to a preferred aspect of the present invention, there is provided a recombinant peptide or mutant thereof which is preferentially immunologically reactive with T cells from individuals with peanut hypersensitivity, which is expressed by the expression of a host cell transformed with a vector coding for the peptide sequence of the present invention. The peptide may be fused to another peptide, polypeptide or protein. Alternatively, the peptide may be prepared by chemical synthetic techniques, such as by the Merrifield solid phase synthesis procedure. Furthermore, although synthetic peptides of the sequence given above represent a preferred embodiment, the present invention also extends to biologically pure preparations of the naturally occurring peptides or fragments thereof. By "biologically pure" is meant a preparation comprising at least about 60%, preferably at least about 70%, or preferably at least about 80% and still more preferably at least about 90% or greater as determined by weight, activity or other suitable means.

The present invention should therefore be understood to encompass peptides that comprise at least one T cell core epitopic region of Ara h 1, as hereinbefore defined, in conjunction with other amino acids (which may or may not be naturally occurring) or other chemical species. In a preferred aspect of the invention such peptides may comprise one or more epitopes of Ara h 1, which epitopes are T cell core epitopic regions. Peptides with one or more epitopes of Ara h 1 are desirable for increased therapeutic effectiveness.

In another aspect, the present invention provides a nucleic acid molecule comprising a sequence of nucleotides encoding or complementary to a sequence encoding the epitopes and peptides as hereinbefore defined or a derivative, homologue or analogue thereof.

It should be understood that reference to "peptides" includes reference to peptides comprising one or more T cell epitopes. A nucleic acid molecule encoding the subject peptide is preferably a sequence of deoxyribonucleic acids such as cDNA or a genomic sequence. A genomic sequence may comprise exons and introns. A genomic sequence may also include a promoter region or other regulatory regions.

The nucleic acid molecule may be ligated to an expression vector capable of expression in a prokaryotic cell (eg. *E.* coli) or a eukaryotic cell (eg. yeast cells, fungal cells, insect cells, mammalian cells or plant cells). The nucleic acid molecule may be ligated or fused or otherwise associated with a nucleic acid molecule encoding another entity such as, for example, a signal peptide. It may also comprise additional nucleotide sequence information fused, linked or otherwise associated with it either at the 3' or 5' terminal portions or at both the 3' and 5' terminal portions. The nucleic acid molecule may also be part of a vector, such as an expression vector. The latter embodiment facilitates production of recombinant forms of the subject peptide which forms are encompassed by the present invention.

Such nucleic acids may be useful for recombinant production of T cell epitopes of Ara h 1 or proteins comprising them by insertion into an appropriate vector and transfection into a suitable cell line. Such expression vectors and host cell lines also form an aspect of the invention.

In producing peptides by recombinant techniques, host cells transformed with a nucleic acid having a sequence encoding a peptide according to the invention or a functional equivalent of the nucleic acid sequence are cultured in a medium suitable for the particular cells concerned. Peptides can then be purified from cell culture medium, the host cells or both using techniques well known in the art such as ion exchange chromatography, gel filtration chromatography, ultrafiltration, electrophoresis or immunopurification with antibodies specific for the peptide.

Nucleic acids encoding Ara h 1 or peptides comprising T cell core epitopic regions of Ara h 1 may be expressed in bacterial cells such as *E. coli*, insect cells, yeast or mammalian cells such as Chinese hamster ovary cells (CHO). Suitable expression vectors, promoters, enhancers and other expression control elements are referred to in Sambruck et al (1989). Other suitable expression vectors, promoters, enhancers and other expression elements are well known to those skilled in the art. Examples of suitable expression vectors in yeast include Yep Sec 1 (Balderi et al., 1987, *Embo J.*, 6:229-234); pMFa (Kurjan and Herskowitz., 1982, *Cell.*, 30:933-943); JRY88 (Schultz et al., 1987, *Gene.*, 54:113-123) and pYES2 (Invitrogen Corporation, San Diego, CA). These vectors are freely available as are baculovirus and mammalian expression systems. For example, a baculovirus system is commercially available (ParMingen, San Diego, CA) for expression in insect cells while the pMsg vector is commercially available (Pharmacia, Piscataway, NJ) for expression in mammalian cells.

For expression in *E. coli* suitable expression vectors include among others, pTrc (Amann et al., 1998, *Gene.*, 69:301-315) pGex (Amrad Corporation, Melbourne, Australia); pMal (N.E. Biolabs, Beverley, MA); pRit5 (Pharmacia, Piscataway, NJ); pEt-11d (Novagen, Maddison, WI) (Jameel et al., 1990, *J. Virol.*, 64:3963-3966) and pSem (Knapp et al., 1990, *Bio Techniques.*, 8:280-281). The use of pTRC, and pEt-11d, for example, will lead to the expression of unfused protein. The use of pMal, pRit5, pSem and pGex will lead to the expression of allergen fused to maltose E binding protein (pMal), protein A (pRit5), truncated-galactosidase (PSEM) or glutathione S-transferase (pGex). When a T cell epitope of Ara h 1 or a peptide comprising it is expressed as a fusion protein, it is particularly advantageous to introduce an enzymatic cleavage site at the fusion junction between the carrier protein and the peptide concerned. The peptide of the invention may then be recovered from the fusion protein through enzymatic cleavage at the enzymatic site and biochemical purification using conventional techniques for purification of proteins and peptides. The different vectors also have different promoter regions allowing constitutive or inducible expression or temperature induction. It may additionally be appropriate to express recombinant peptides in different *E. coli* hosts that have an altered capacity to degrade recombinantly expressed proteins. Alternatively, it may be advantageous to alter the nucleic acid sequence to use codons preferentially utilised by *E. coli*, where such nucleic acid alteration would not effect the amino acid sequence of the expressed proteins.

Host cells can be transformed to express the nucleic acids of the invention using conventional techniques such as calcium phosphate or calcium chloride co-precipitation, DEAE-dextran-mediated transfection or electroporation. Suitable methods for transforming the host cells may be found in Sambruck et al. (1989), and other laboratory texts. The nucleic acid sequence of the invention may also be chemically synthesised using standard techniques.

In addition to recombinant production of peptides according to the invention, the nucleic acids may be utilised as probes for experimental or purification purposes.

Identification and synthesis of the Ara h 1 T cell epitopes as disclosed herein now facilitates the development of a range of diagnostic and prophylactic/therapeutic treatment protocols for use with respect to peanut related immune conditions. Also facilitated is the development of reagents for use therein. Accordingly, the present invention should be understood to extend to the use of the peptides or functional derivatives, homologues or analogues thereof in the therapeutic and/or prophylactic treatment of patients. Such methods of treatment include, but are not limited to:

(i) Administration of the subject peptides or mutants thereof to a patient as a means of desensitising or inducing immunological tolerance to Ara h 1 or Ara h 1-like molecules. This may be achieved, for example, by inducing Ara h 1 directed Th2 anergy or apoptosis. Such an outcome may be achieved by any one of a number of techniques including the use of peptides which maintain T cell epitope reactivity but which either naturally or as a result of mutation are unable to undergo IgE binding. Alternatively, one may utilise desensitisation/treatment protocols which are based on the administration of specific concentrations of a given peptide in accordance with a specific regimen in order to induce tolerance. Such methodology may eliminate Ara h 1 hypersensitivity or it may reduce the severity of Ara h 1 hypersensitivity or sensitivity to an allergen present in a composition comprising Ara h 1, such as a peanut allergy. Reference herein to the treatment of Ara h 1 sensitivity should be understood to encompass within its scope the treatment of conditions characterised by sensitivity to compositions which comprise Ara h 1, such as peanuts generally, even if the sensitivity is directed to an allergen other than Ara h 1.

Preferably such treatment regimens are capable of modifying the T cell response or both the B and T cell response of the individual concerned. As used herein, modification of the allergic response of the individual suffering from peanut hypersensitivity can be defined as inducing either non-responsiveness or diminution in symptoms to the Ara h 1 molecule as determined by standard clinical procedures (Varney et al. 1991 *British Medical Journal* 302:265-269). Diminution in the symptoms includes any reduction in an allergic response in an individual to Ara h 1 after a treatment regime has been completed. This diminution may be subjective or clinically determined, for example by using standard skin tests known in the art.

Exposure of an individual to the peptides of the present invention, which peptides comprise at least one T cell epitope, may tolerise or anergise appropriate T cell subpopulations such that they become unresponsive to Ara h 1 and do not participate in stimulating an immune response upon such exposure. Preferably the peptides according to the invention will retain immunodominant T cell epitopes but possess abrogated IgE binding. Still further, even if the allergen in issue is not Ara h 1, but is directed to a different allergen which is present in the same composition as Ara h 1 (such as a different peanut allergen) immunisation with Ara h 1 may nevertheless induce a bystander suppressive effect which acts to reduce the degree of hypersensitivity to that allergen.

Administration of a peptide of the invention may modify the cytokine secretion profile as compared with exposure to naturally occurring Ara h 1 allergen. This exposure may also influence T cell subpopulations which normally participate in the allergic response to migrate away from the site or sites of normal exposure to the allergen and towards the site or sites of therapeutic administration. This redistribution of T cell subpopulations may ameliorate or reduce the ability of an individual's immune system to stimulate the usual immune response at the site of normal exposure to the allergen, resulting in diminution of the allergic symptoms.

Modification of the B cell response may be achieved, for example, via modulation of the cytokine profile produced by T cells, as detailed above. Specifically, decreasing T cell derived IL-4 and IL-13 production thereby decreasing IgE synthesis.

(ii) The peptides of the present invention may be used in the capacity of an adsorbent to remove Ara h 1 directed T cells from a biological sample or from a patient.

Accordingly, in another aspect the present invention provides a method for the treatment and/or prophylaxis of a condition in a subject, which condition is characterised by the aberrant, unwanted or otherwise inappropriate immune response to Ara h 1 or an allergen in a composition comprising Ara h 1, said method comprising administering to said subject an effective amount of a composition as hereinbefore defined for a time and under conditions sufficient to remove or reduce the presence or function in said subject of T cells directed to said Ara h 1 or other allergen.

Preferably said condition is hypersensitivity to peanuts or tree nuts which contain Ara h 1 or Ara h 1-like molecules, such as hazelnuts, almonds or Brazil nuts.

In one embodiment, said method desensitises or induces immunological tolerance to Ara h 1 or other allergen of said composition.

In another embodiment, said desensitization or tolerance is achieved by inducing Th2 anergy or apoptosis.

In still another embodiment, said desensitisation or tolerance is achieved by inducing Ara h 1-specific Treg cells.

An "effective amount" means an amount necessary at least partly to attain the desired immune response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

It should also be understood that the composition of the present invention may exclusively comprise Ara h 1 epitopes or it may also comprise other epitopes or molecules useful for achieving therapeutic efficacy, such as a range of Ara h 2 epitopes.

The subject of the treatment or prophylaxis is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably the mammal is a human or primate. Most preferably the mammal is a human.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

Administration of the peptide of the present invention (herein referred to as "agent") in the form of a pharmaceutical composition, may be performed by any convenient means. The agent of the pharmaceutical composition is contemplated to exhibit therapeutic activity when administered in an amount which depends on the particular case. The variation depends, for example, on the human or animal and the agent chosen. A broad range of doses may be applicable. Considering a patient, for example, from about 0.1 mg to about 1 mg of an agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation.

The agent may be administered in a convenient manner such as by the oral, intravenous (where water soluble), intraperitoneal, intramuscular, subcutaneous, intradermal, intranasal, sublingual or suppository routes or implanting (e.g. using slow release molecules). The agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order.

Another aspect of the present invention contemplates the use of a composition as hereinbefore defined in the manufacture of a medicament for the treatment of a condition in a mammal, which condition is characterised by an aberrant, unwanted or otherwise inappropriate immune response to Ara h 1.

Figure 4:
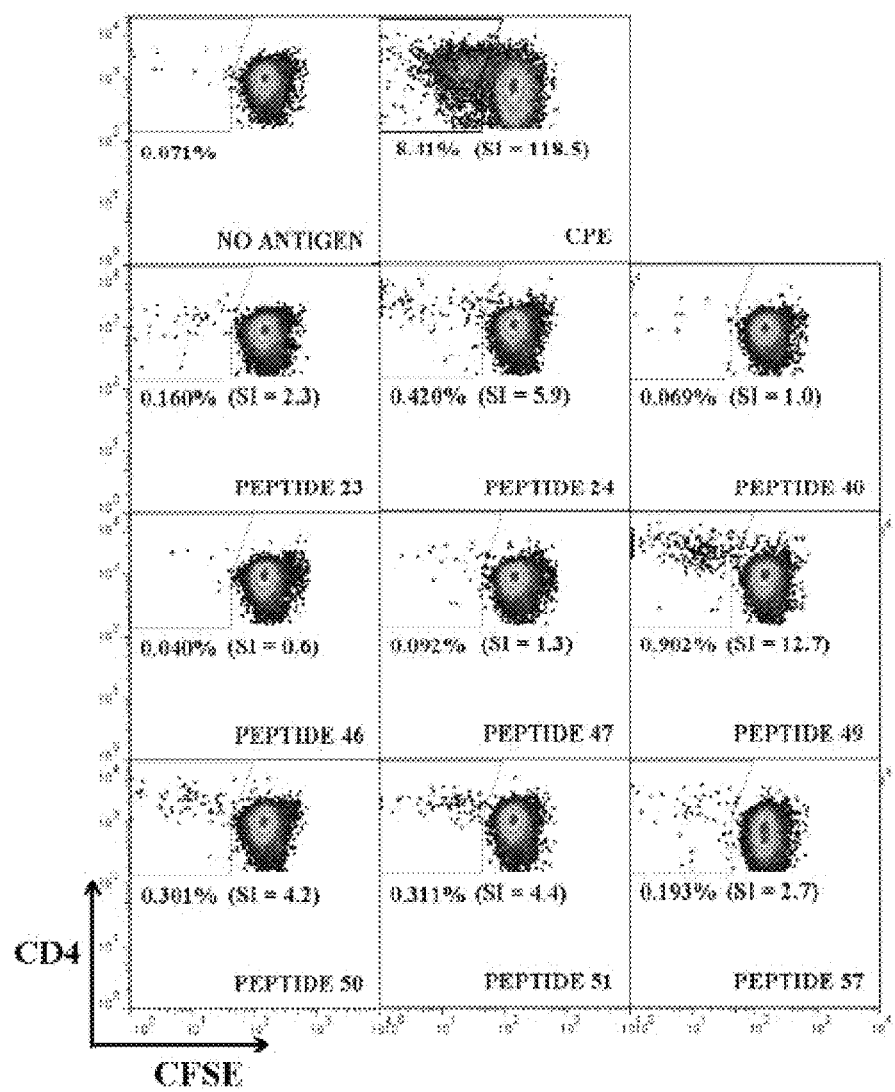
FIG. 4: Representative CFSE-based assay for detecting CD4+ T-cell proliferation in PBMC Proliferation of CFSE-labelled PBMC from peanut-allergic subject 26 following 7 days stimulation with selected Ara h 1 20-mer peptides. Medium alone (No Antigen) or crude peanut extract (CPE) provided negative and positive controls respectively. At least 10,000 live CD4+ T cells were analyzed per sample. Gates indicate percentage CD4+CFSE$^{lo}$ (proliferating) T cells of total CD4+ T cells with stimulation indices (SI) in parentheses.

Preferably said condition is hypersensitivity to peanuts or a tree nut which contains Ara h 1 or Ara h 1-like molecules, such as a hazelnut.

In yet another further aspect, the present invention contemplates a pharmaceutical composition comprising a composition as hereinbefore defined together with one or more pharmaceutically acceptable carriers and/or diluents. Said composition is referred to as the active ingredients.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 μg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule encoding a modulatory agent. The vector may, for example, be a viral vector.

Routes of administration include, but are not limited to, respiratorally (eg. intranasally or orally via aerosol), intratracheally, nasopharyngeally, intravenously, intraperitoneally, subcutaneously, intracranially, intradermally, intramuscularly, intraoccularly, intrathecally, intracereberally, intranasally, infusion, orally, rectally, via IV drip patch, implant and sublingual. Preferably, said route of administration is subcutaneously, intradermally or intranasally.

Yet another aspect of the present invention relates to the compositions, as hereinbefore defined, when used in the method of the present invention.

In yet another aspect, the present invention should be understood to extend to the use of the epitopes and peptides of the present invention in diagnostic applications. Said diagnostic applications include, but are not limited to:

(i) To measure the reactivity of a subject's cells to Ara h 1. This is of use, for example, with respect to the diagnosis and/or monitoring of conditions characterised by an aberrant, unwanted or otherwise inappropriate immune response to Ara h 1. The peptides may be added into solution or bound to a solid support together with cells derived from peripheral blood or from tissue biopsies either unfractionated, fractionated or derived as a continuous cell line. Reactivity to the subject peptide may then be measured by standard proliferation assays such as incorporation of $H^3$-thymidine, measurement of expressed or secreted molecules such as surface markers, cytokines or other standard assays of cellular activity which are well known in the art.

(ii) The use of T cell epitope comprising peptides together with a T cell proliferation assay which utilises a T cell sample derived from the subject will facilitate, for example, the identification of a T cell responsive population.

Methods of detecting Ara h 1 may be utilised, for example, to qualitatively or quantitatively detect Ara h 1 levels. However, these methods may also be utilised to screen for mutations or polymorphisms in Ara h 1 which mutations may result in, for example, loss of T cell reactivity to Ara h 1. These methods may be utilised for the purpose of screening for peptide molecules suitable for use in therapeutically or prophylactically treating an individual suffering from Ara h 1 related hypersensitivity.

Accordingly, yet another aspect of the present invention is directed to a method of diagnosing or monitoring a condition in a mammal, which condition is characterised by an aberrant, unwanted or inappropriate response to Ara h 1, said method comprising screening for Ara h 1 reactive T cells utilising the peptides or epitopes hereinbefore defined.

Preferably said condition is hypersensitivity to peanuts or tree nuts which contain Ara h 1 or Ara h 1-like molecules, such as hazelnuts, almonds or Brazil nuts.

In another embodiment the present invention provides diagnostic kits for use in the diagnostic methodology hereinbefore defined.

The present invention will now be further described with reference to the following non-limiting Examples.

EXAMPLES

Methods

Subjects

Peanut-allergic adult subjects were recruited from The Alfred Allergy Clinic, Melbourne, Australia (Table 3). All subjects had clinical symptoms of IgE-mediated peanut allergy and peanut-specific IgE CAP score >1 (>0.49 $kU_A$/1; Pharmacia CAP System™, Pharmacia Diagnostics, Uppsala, Sweden). Subjects used for T-cell line (TCL) generation were genotyped (HLA-DRB 1, -DQB 1 and -DPB 1, exon 2) by the Victorian Transplantation and Immunogenetics Service (Table 4). The study was approved by The Alfred and Monash University Ethics Committees and informed written consent obtained from each subject.

Antigens

Crude peanut extract (CPE) was prepared from commercial unsalted, dry-roasted peanuts as described (Prickett et al. 2011 supra; de Leon et al. *Clin Exp Allergy.* 2003; 33(9):1273-80). Ara h 1 and Ara h 1 were enriched from CPE by liquid chromatography as described (Prickett et al. 2011 supra). Endotoxin contents were 1.7, 4.0 and 78.0 EU/mg for CPE, Ara h 1 and Ara h 1 respectively (Endpoint Chromogenic LAL assay, Lonza, Walkersville, USA). Ara h 1 peptides (Mimotopes, Victoria, Australia and GenScript USA Inc, New Jersey, USA; Table 5) were reconstituted at 2 mg/ml in 10% dimethyl sulfoxide/PBS (20-mers and truncated peptide sets) or PBS alone (custom-synthesized core epitope peptides). All antigens were confirmed to be neither mitogenic nor toxic as described (Eusebius et al. *Int Arch Allergy Immunol.* 2002; 127(3):234-44).

Generation of Ara h 1-specific $CD4^+$ T-cell lines (TCL)

Ara h 1-specific oligoclonal TCL were generated from peripheral blood mononuclear cells (PBMC) of peanut-allergic subjects using 5,6-carboxyfluorescein diacetate succinimidylester (CFSE)-based methodology (Mannering et al. *J Immunol Methods.* 2005; 298(1-2):83-92) as described (Prickett et al. 2011 supra), with CPE (100 pg/mL), Ara h 1 (10 gg/mL) or 20-mer peptides spanning the Ara h 1 sequence (11 amino acid (aa) overlap (17 aa overlap for the last peptide); Table 5; 10 pg/mL/peptide) as the driving antigens. All TCL were tested for specificity (proliferation) to individual Ara h 1 20-mers (10 pg/mL) as well as CPE (100 pg/mL) and/or Ara h 1 (10 pg/mL) Core epitope sequences were mapped within selected 20-mers using peptide sets truncated from the N- or C-terminus of the 20-mer as described (Prickett et al. 2011 supra).

T-Cell Assays

All culturing was performed in RPMI-1640 containing 2 mM L-glutamine, 100 IU/mL penicillin-streptomycin and 5% heat-inactivated human AB serum (Sigma-Aldrich, St Louis, USA) (cRPMI). Antigen-induced TCL proliferation was assessed by $^3$H-thymidine (3H-TdR) uptake assays as described (Prickett et al. 2011 supra). A stimulation index (SI; cpm antigen-stimulated T cells/cpm unstimulated T cells) >2.5 was considered positive and all positive responses confirmed in >2 assays. HLA-restriction of epitope recognition by TCL was assessed using monoclonal antibodies (mAb) against HLA-DR (L243), HLA-DQ (SVP-L3) or HLA-DP (B7/21) to block epitope presentation as described (Prickett et al. 2011 supra). To allow detection of peptide-induced CD4+ T-cell proliferation within whole PBMC, 7-day cultures of CFSE-labelled PBMC were set up as described for TCL generation (Prickett et al. 2011 supra). At least 10,000 $CD4^+$ T cells were analyzed per sample and SI calculated as percentage of $CD4^+CFSE^{lo}$ (proliferated) cells with antigen/percentage of $CD4^+CFSE^{lo}$ cells without antigen (background). The detection threshold for a specific response in this assay was assessed by expanding peptide-specific TCL from proliferated $CD4^+$ cells over a range of SI values for three subjects. Specific TCL could be generated from divided T cells with SI as low as 1.1 in all three subjects (data not shown) allowing designation of an SI>1.1 as positive.

Basophil Activation Test

Basophil activation was assessed by CD63 upregulation detected by flow cytometry as described (Drew et al. *J Immunol.* 2004; 173(9):5872-9). Positive controls were rabbit anti-human IgE antibody (7.5 ug/mL; DAKO Corporation, CA, USA), N-formyl-methionine-leucine-phenylalanine (fMLP) (0.4 ug/mL; Sigma) and CPE. CPE, Ara h 1 and peptides were tested over a 3-log concentration range (5, 0.5 and 0.05 ug/mL)

Results

Selection of Ara h 1 20-Mer Peptides Containing Dominant $CD4^+$ T-Cell Epitopes Recognized by Peanut-Allergic Subjects A total of 145 Ara h 1-specific T-cell lines (TCL) were generated from PBMC of 18 HLA-diverse peanut-allergic subjects (Table 3 and 4) by isolating and expanding antigen-specific (proliferated) $CD4{\pm}CFSE^{lo}$ T cells from 7-day CFSE-labelled PBMC cultures stimulated with CPE, Ara h 1 or pools of Ara h 1 20-mer peptides collectively spanning the Ara h 1 sequence (Table 5). The 20-mer peptide(s) recognized (SI≥2.5) by each subject are shown in FIG. 9 and data summarized in FIG. 1. For some subjects, CPE or Ara h 1 stimulation generated most TCL whilst for others it was the peptide pools. Where TCL were generated from a given subject using different antigen preparations (CPE, Ara h or peptide pools), TCL 20-mer specificities were comparable. Overall, there was no bias in the TCL 20-mer specificity generated depending on antigen preparation.

The 145 TCL collectively recognized epitopes throughout the entire Ara h 1 sequence, with only four of the sixty-nine 20-mers failing to stimulate any TCL. Fourteen 20-mers (23, 24, 26, 38, 40, 44-51 and 57) were each recognized by four (22%) or more subjects, with peptides 50 and 51 having the most responders (six subjects; 33%) (FIG. 1). In order to select 20-mers containing dominant T-cell epitopes, a number of factors were considered in addition to responder frequencies, including magnitude of TCL response, number of specific TCL per subject, reproducibility of specific TCL response and ability to target specific T cells in PBMC. Based on these parameters, nine of the fourteen 20-mers (peptides 23, 24, 40, 46, 47, 49, 50, 51 and 57) were selected for subsequent analyses. These nine 20-mers were collectively recognized by 16 of the 18 subjects (89%) in this cohort, and typically induced strong and consistent proliferative responses in specific TCL, with the majority of SI over five and many considerably higher (FIG. 9). Furthermore, each of these 20-mers was recognized by multiple TCL from many responders reflecting a prevalence of T cells specific for these peptides among the subjects' T-cell repertoires. To assess recognition in a wider cohort, PBMC from an additional 21 peanut-allergic subjects were screened by CFSE assay for $CD4^+$ T-cell proliferation in whole PBMC following seven days stimulation with each peptide (FIG. 6, upper panel and FIG. 4). This assay provided a sensitive and accurate screen for detecting peptide-specific $CD4^+$ T cell responses within whole PBMC. All 21 subjects showed PBMC T-cell proliferation to CPE or a combination of enriched Ara h 1 and Ara h 1. The 20-mers were collectively recognized by 19 (90 of these subjects, with 8-12 (38-60%) responders per 20-mer. Analysis of four subjects from the original cohort used for TCL generation confirmed they also had T cells specific for other 20-mers in addition to those recognized by their TCL (FIG. 6, lower panel). Overall, T-cell recognition of the selected panel of nine 20-mers was confirmed in 35 (90%) of 39 subjects analyzed.

Mapping Core T-Cell Epitopes within Selected Ara h 1 20-Mer Peptides

Minimal length peptides decrease risk of cross-linking cell-bound IgE on inflammatory cells during clinical administration and facilitate therapeutic production. The minimum T-cell stimulatory sequence (core epitope) within each selected 20-mer was determined by testing proliferation of reactive TCL from different subjects to truncated peptide sets (e.g. FIG. 2 and FIG. 7). The number of residues required to induce maximal T-cell proliferation varied from 6-19 aa between different TCL and/or subjects (FIG. 7), consistent with previous reports for $CD4^+$ T-cell epitopes (Hemmer et al. *Int Immunol.* 2000; 12(3):375-83 (Hemmer et al. *Int Immunol.* 2000; 12(3):375-83; Suri et al. *Curr Opin Immunol.* 2006; 18(1):70-7). Due to variation in the number of flanking-residues required for optimal epitope recognition (Suri et al. 2006 supra), TCL were considered to recognize the same epitope if peptides containing a common core sequence induced recognition. Based on this criterion, ten distinct $CD4^+$ T-cell epitopes were identified ('consolidated epitopes', FIG. 7), with common cores varying from 5-12 aa (underlined sequences, FIG. 7). 'Consolidated epitope' sequences were selected to encompass residues required for maximal stimulation of all specific TCL tested to ensure broadest possible recognition.

Figure 2:
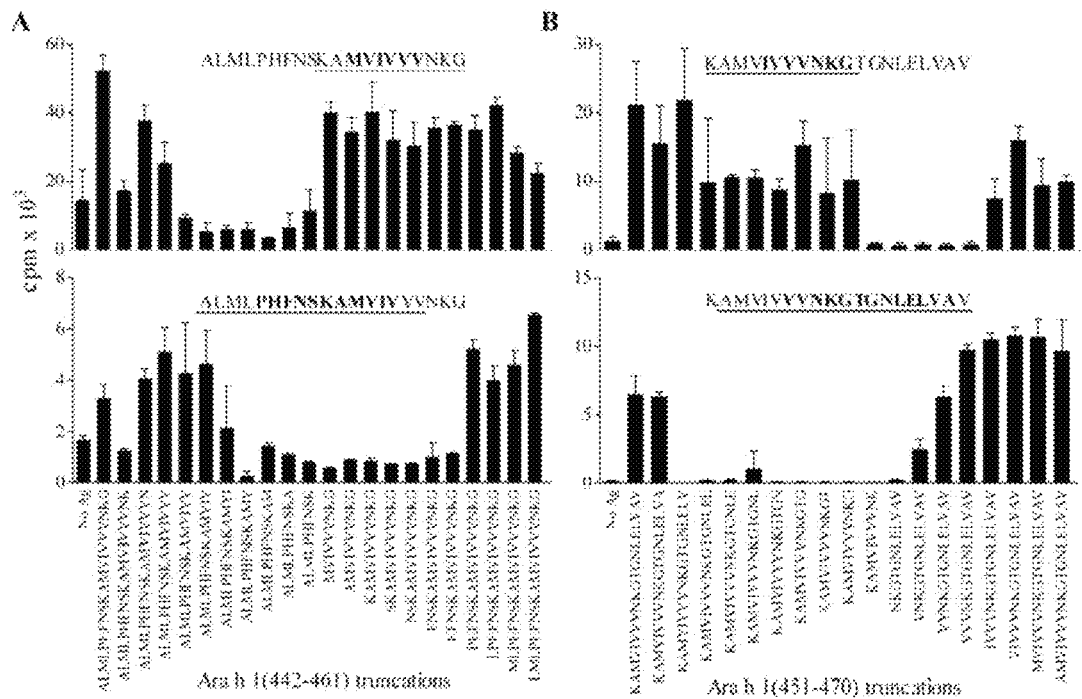
FIG. 2: Mapping core T-cell epitopes within Ara h 1 20-mer peptides 50 and 51 20-mer-specific TCL proliferation to truncated peptide sets. Representative TCL shown for peptides 50 (A) and 51 (B) (mean cpm replicate wells+SD). Upper panels indicate the epitope in overlap between the 20-mers (n=2; 3 TCL). Lower panels indicate epitopes unique to each 20-mer; A) n=3; 6 TCL. B) n=4; 7 TCL. Epitope sequences recognized by represented TCL are bolded and 'consolidated epitopes' recognized by all specific TCL are underlined.
Figure 10:
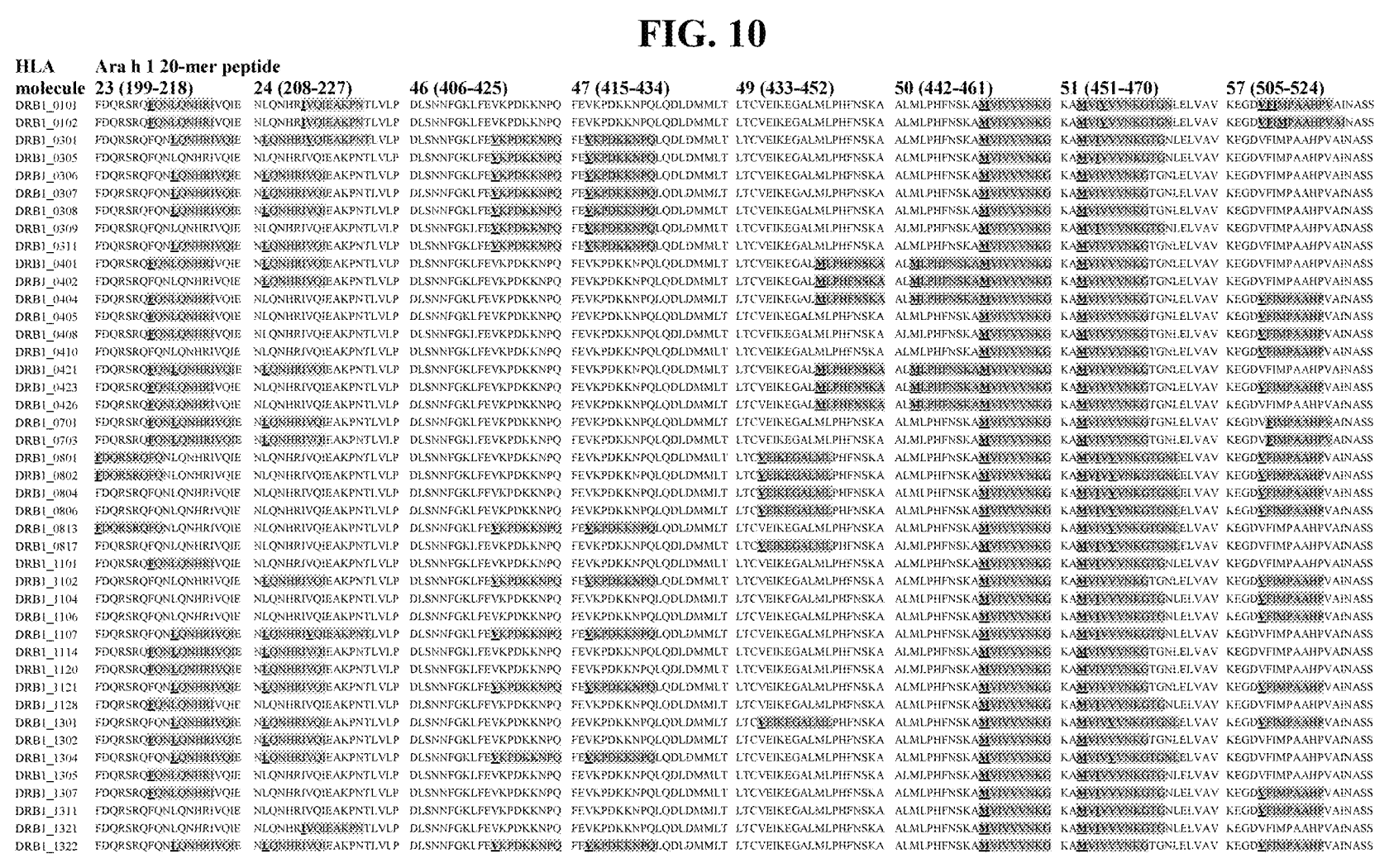

At least one epitope was found within each of the nine 20-mers, with 20-mers 50 and 51 each containing two distinct but overlapping T-cell epitopes: one unique to each 20-mer ((442-458) and (452-470)), and the other within the overlap sequence ((451-461), FIG. 7 and FIG. 2). No single TCL responded to both epitopes within either 20-mer, further confirming the distinction of these epitopes (data not shown). HLA-epitope prediction algorithms (Singh et al. *Bioinformatics.* 2001; 17(12):1236-7; Vita et al. *Nucleic Acids Res.* 2010; 38 (Database issue):D854-62) also highlighted one or more strong HLA class II (HLA-II) binding motifs within each of our minimal-stimulatory sequences. Data are shown for the Propred (Singh et al. 2001 supra) HLA-DR binding algorithm in FIG. 10. This algorithm did not predict HLA-DR epitopes within peptide 40, but algorithms of the Immune Epitope Database (IEDB) and Analysis Resource (Vita et al. 2010, supra) predicted epitopes within this peptide to bind most strongly to HLA-DP and/or -DQ molecules.

Finally, to avoid unnecessary sequence duplication and to minimize peptide numbers for a therapeutic, six of the consolidated epitopes (comprising three overlapping epitope pairs) were combined into three single peptides of 20 aa or less ((206-225), (409-427) and (451-470); grey shading, FIG. 7). The combined epitope peptides efficiently stimulated TCL specific for either epitope (data not shown) and together with the remaining four consolidated epitopes ((353-371), (436-452), (442-458) and (507-524)), provided a panel of seven candidate peptides for further characterization (see asterisks, Table II). CFSE-based screening of nine subjects from our cohorts confirmed that these peptides could each directly target detectable numbers of Ara h 1-specific T cells among whole PBMC of peanut-allergic subjects (FIG. 11).

Determining HLA Class II Restriction Specificity of Ara h 1 T-Cell Epitopes

Figure 5:
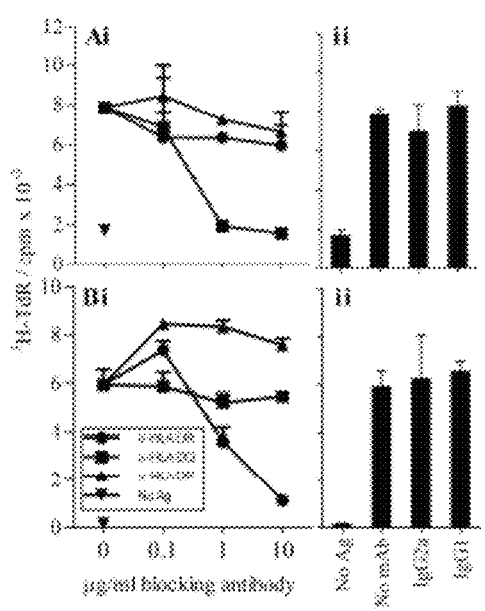
FIG. 5: Representative HLA class II restriction specificity of T-cell epitope recognition Proliferation of specific TCL to selected epitopes in the presence of HLA-DR (circles), -DQ (squares) or -DP (triangles) mAbs (Ai and Bi) or isotype control antibodies (10 ug/ml) (Aii and Bii), (mean cpm replicate wells+SD). Graphs show sample data for an HLA-DR-restricted epitope (442-458) (A) and an HLA-DQ restricted epitope (507-524) (B).
Figure 9:
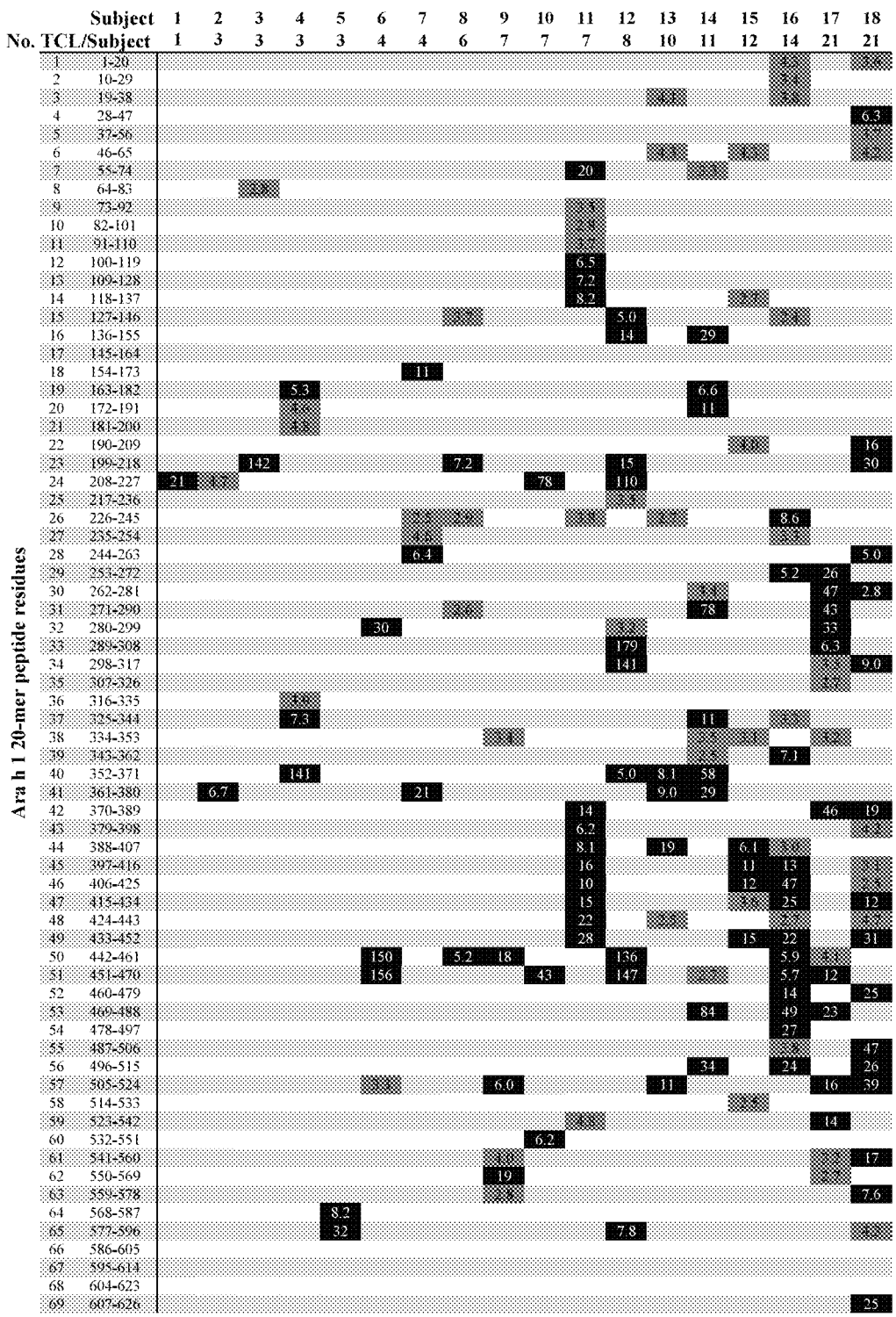
FIG. 9 is a table showing proliferative responses (thymidine uptake) of T-cell lines to Ara h 1 20-mer peptides. TCL, T-cell line. Only positive stimulation indices (SI >2.5) are shown. For subjects with multiple TCL specific for a given 20-mer, the highest SI is shown. SIs above 10 have been rounded to the nearest whole number. Dark grey, SI >2.5<5.0; Black, SI >5.0.

There is no identified HLA-II association with peanut allergy (Shreffler et al. *Ann Allergy Asthma Immunol* 2006; 96(6):865-9), therefore peptides selected for therapy must bind diverse HLA-II molecules for wide applicability. To determine the HLA-II type presenting each epitope, anti-HLA-DR, -DP or -DQ mAbs were used to block individual epitope presentation to T cells. For each TCL tested, epitope recognition was prevented by one or more HLA-mAb in a dose-dependent manner (e.g. FIG. 5) and the same mAb blocked recognition of CPE (data not shown), demonstrating consistency for presentation of naturally processed and synthetic epitope forms. At least two subjects and/or TCL were tested per epitope (FIG. 8). Consistent with predictions of the HLA-II algorithms described above (Singh et al. 2001 supra; Vita et al. 2010 supra), anti-HLA-DR blocked recognition of all but one epitope, (353-371), which was blocked by anti-HLA-DQ in both subjects tested. For epitopes (436-452) and (507-524), recognition was blocked by anti-HLA-DR for some TCL but by anti-HLA-DQ for others, confirming HLA-binding degeneracy for these epitopes.

To assess HLA-binding degeneracy of epitopes whose recognition was blocked by a single HLA-mAb, the respective HLA-alleles of at least two subjects with TCL specific for that epitope were compared (Table 4 and FIG. 8). The absence of shared HLA-DRB1 or HLA-DQB1 alleles between subjects recognizing HLA-DR- or HLA-DQ-restricted epitopes respectively confirmed that each epitope was presented on at least two different HLA-molecules. The HLA-binding algorithms further supported these data, with each epitope containing motifs predicted to bind multiple HLA-molecules ((Singh et al. 2001 supra; Vita et al. 2010 supra) (e.g. FIG. 10).

Testing Candidate Peptides for Basophil Activation

Figure 3:
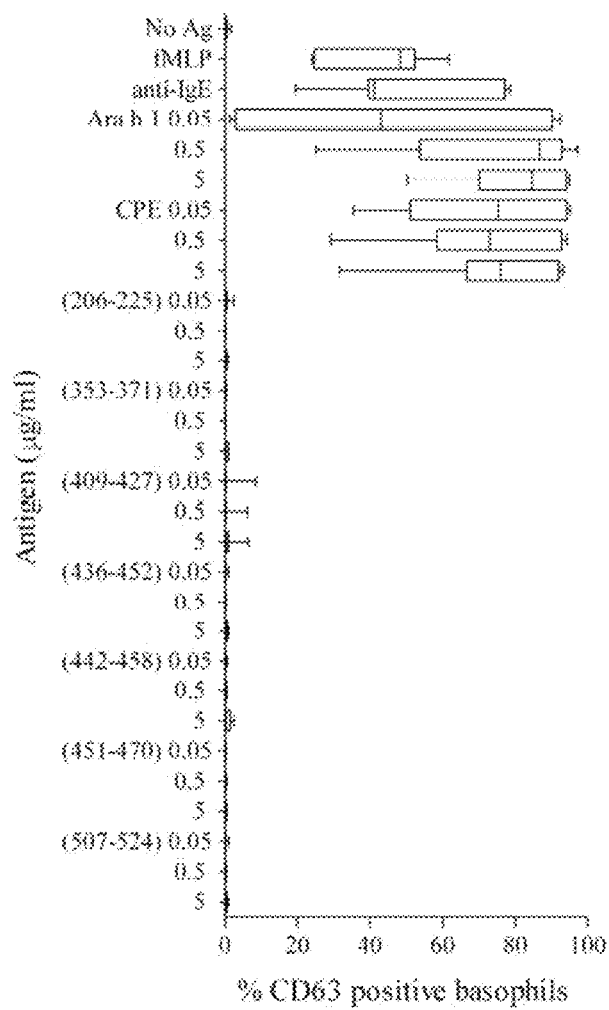
FIG. 3: Basophil activation in response to candidate Ara h 1 peptides Box-and-whiskers plot showing percentage of activated ($CD63^{hi}$) basophils ($IgE^{hi}$) in response to Ara h 1 or candidate peptides for seven peanut-allergic subjects. Negative control was no antigen (unstimulated) and positive controls were anti-IgE, fMLP and CPE. Whiskers show minimum to maximum values.

To provide a safe alternative to whole allergens, peptides must not bind and cross-link cell-bound IgE. Basophil reactivity to peptides was assessed in fresh blood from seven of the peanut-allergic subjects recruited for this study (Table 3) (FIG. 3). All seven subjects showed high levels of basophil activation to CPE over a concentration range. Whilst responses to Ara h 1 varied between subjects at the lowest dose, the highest concentration induced high activation in all subjects. However, none of the candidate peptides induced activation at any concentration tested. One subject showed a very low response (8%) to peptide (409-427), but this was below the threshold of positive activation (Boumiza et al. *Clin Mol Allergy.* 2005; 3:9) and was negligible compared to the activation induced by Ara h 1 (80-90%) or CPE (74-76%) in this subject.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

Subject demographics

| | | | | | Peanut | | Use of patient samples | | | |
|---|---|---|---|---|---|---|---|---|---|---|
| Subject | Sex | Age | Atopic | Asthma | CAP kU$_A$/l (score) | Anaphylaxis | TCL | 20-mer CFSE | Core CFSE | BAT |
| 1 | M | 39 | Yes | No | 2.18 (2) | Yes | X | X | X | |
| 2 | M | 34 | Yes | Yes | 0.78 (2) | Yes | X | X | | |
| 3 | F | 53 | Yes | as a child | 83.90 (5) | Yes | X | | | |
| 4 | F | 19 | Yes | No | 98.90 (5) | Yes | X | X | | |
| 5 | F | 22 | Yes | No | 4.72 (3) | Yes | X | | | |
| 6 | M | 30 | Yes | No | 17.00 (4) | Yes | X | | | |
| 7 | M | 42 | No | No | 15.40 (3) | Yes | X | | | |
| 8 | M | 36 | Yes | Yes | 56.60 (5) | Yes | X | | | |
| 9 | M | 30 | Yes | Yes | 30.60 (4) | Yes | X | | | |
| 10 | M | 37 | Yes | Yes | 42.70 (4) | Yes | X | X | | X |
| 11 | F | 26 | Yes | Yes | 2.82 (2) | Yes | X | | | |
| 12 | F | 23 | Yes | Yes | >100 (6) | Yes | X | | | |
| 13 | M | 30 | Yes | No | >100 (6) | Yes | X | | | |
| 14 | M | 30 | Yes | Yes | 36.60 (4) | Yes | X | | | X |
| 15 | F | 31 | Yes | No | 84.30 (5) | No | X | | | |
| 16 | F | 20 | Yes | Yes | 1.16 (2) | Yes | X | | | |
| 17 | F | 25 | Yes | No | 2.12 (2) | Yes | X | | | X |
| 18 | M | 35 | Yes | Yes | 1.23 (2) | No | X | | | |
| 19 | M | 27 | Yes | Yes | 6.19 (3) | Yes | | X | | |
| 20 | F | 25 | Yes | Yes | 87.2 (5) | Yes | | X | | |
| 21 | F | 53 | Yes | No | 1.43 (2) | No | | X | | |
| 22 | F | 28 | Yes | Yes | 9.53 (3) | na | | X | | |
| 23 | F | 37 | Yes | No | 6.94 (3) | Yes | | X | | |
| 24 | M | 38 | Yes | Yes | 2.42 (2) | Yes | | X | | |
| 25 | M | 28 | Yes | Yes | >100 (6) | Yes | | X | | |
| 26 | F | 70 | No | No | 2.18 (2) | Yes | | X | | X |
| 27 | F | 26 | Yes | No | 1.37 (2) | No | | X | | |
| 28 | F | 35 | Yes | No | SPT 14 mm | Yes | | X | | |
| 29 | F | 23 | na | No | 2.37 (2) | na | | X | | |
| 30 | F | 28 | Yes | Yes | 9.2 (3) | No | | X | X | |
| 31 | F | 30 | Yes | Yes | 10.20 (3) | Yes | | X | X | |
| 32 | M | 53 | Yes | No | 2.01 (2) | Yes | | X | X | |
| 33 | M | 26 | Yes | Yes | 12.00(3) | Yes | | X | X | |
| 34 | M | 43 | Yes | Yes | 1.63 (2) | No | | X | X | X |
| 35 | F | 33 | Yes | na | 0.49 (1) | No | | X | X | |
| 36 | F | 52 | Yes | Yes | 7.23 (3) | Yes | | X | X | X |
| 37 | M | 28 | Yes | na | 0.72 (2) | No | | X | X | |
| 38 | F | 21 | Yes | Yes | 1.51 (2) | Yes | | X | | |
| 39 | M | 28 | Yes | Yes | 1.43(2) | Yes | | X | | |
| 40 | M | 29 | Yes | No | 31.80 (4) | Yes | | | | X |

TCL, T cell line; 20-mer CFSE, screen for T cell reactivity to selected Ara h 1 20-mers; Core CF SE, screen for T cell reactivity to candidate Ara h 1 peptides; BAT, basophil activation test; na, data not available; SPT, skin-prick test (RAST not available for this subject).

TABLE 4

HLA genotyping for subjects used for T-cell line generation

| | HLA-genotypes | | | | | |
|---|---|---|---|---|---|---|
| Subject | DRB1 | | DQB1 | | DPB1 | |
| 1 | 07:01 | 15:01 | 02:01 | 06:02 | 04:01 | |
| 2 | 01:01 | 03:01 | 05:01 | 06:02 | 04:01 | 04:02 |
| 3 | 03:01 | 08:01 | 02:01P | 04:02 | 03:01P | 04:01 |
| 4 | 11:01 | 15:01 | 03:01P | 06:02 | 04:01 | |
| 5 | 11:01 | 15:01 | 03:01P | 06:02 | 03:01P | 04:01 |
| 6 | 04:01 | 04:04 | 03:02 | 04:02 | 13:01P | 04:01 |
| 7 | 07:01 | 08:01 | 03:03 | 04:02 | 04:01 | 06:01 |
| 8 | 01:03 | 04:01 | 03:02 | 05:01 | 03:01P | 02:01 |
| 9 | 09:01 | 13:01 | 03:03 | 06:03 | 03:01P | 04:02P |
| 10 | 11:01 | 15:01 | 03:01P | 06:02 | 04:01 | |
| 11 | 03:01 | 13:02 | 02:01P | 06:09 | 01:01 | 04:01 |
| 12 | 08:01 | 10:01 | 04:02 | 05:01 | 03:01P | 04:01 |
| 13 | 12:01P | 15:01 | 03:01 | 06:02 | 13:01P | 04:01 |
| 14 | 13:02 | | 06:09 | | 05:01 | 04:02P |
| 15 | 03:01P | 04:01 | 04:01P | | 02:01P | 03:01P |

TABLE 4-continued

HLA genotyping for subjects used for T-cell line generation

| | HLA-genotypes | | | | | |
|---|---|---|---|---|---|---|
| Subject | DRB1 | | DQB1 | | DPB1 | |
| 16 | 04:04 | 13:01 | 03:02 | 06:03 | 02:01 | 04:01 |
| 17 | 11:04 | 15:01 | 03:01P | 06:02 | 02:01 | 14:01 |
| 18 | 04:05 | 15:01 | 03:02 | 06:02 | 03:01P | 04:01 |

All HLA abbreviations comply with recent changes to allele nomenclature (http:/hla.alleles.org/announcement.html and http://www.ebi.ac.uldimgt/h1a/).

Alleles followed by a I$^v$ represent groups of alleles that share common sequences in exon 2 (http://hla.alleles.org/alleles/p_groups.html).

TABLE 5

Ara h 1 20-mer peptides

| Pool | No. | Residues | Sequence |
|---|---|---|---|
| 1 | 1 | 1-20 | MRGRVSPLMLLLGILVLASV |
| | 2 | 10-29 | LLLGILVLASVSATHAKSSP |
| | 3 | 19-38 | SVSATHAKSSPYQKKTENPC |

TABLE 5-continued

Ara h 1 20-mer peptides

| Pool | No. | Residues | Sequence |
|---|---|---|---|
|  | 4 | 28-47 | SPYQKKTENPCAQRCLQSCQ |
|  | 5 | 37-56 | PCAQRCLQSCQQEPDDLKQK |
|  | 6 | 46-65 | CQQEPDDLKQKACESRCTKL |
|  | 7 | 55-74 | QKACESRCTKLEYDPRCVYD |
| 2 | 8 | 64-83 | KLEYDPRCVYDPRGHTGTTN |
|  | 9 | 73-92 | YDPRGHTGTTNQRSPPGERT |
|  | 10 | 82-101 | TNQRSPPGERTRGRQPGDYD |
|  | 11 | 91-110 | RTRGRQPGDYDDDRRQPRRE |
|  | 12 | 100-119 | YDDDRRQPRREEGGRWGPAG |
|  | 13 | 109-128 | REEGGRWGPAGPREREREED |
|  | 14 | 118-137 | AGPREREREEDWRQPREDWR |
| 3 | 15 | 127-146 | EDWRQPREDWRRPSHQQPRK |
|  | 16 | 136-155 | WRRPSHQQPRKIRPEGREGE |
|  | 17 | 145-164 | RKIRPEGREGEQEWGTPGSH |
|  | 18 | 154-173 | GEQEWGTPGSHVREETSRNN |
|  | 19 | 163-182 | SHVREETSRNNPFYFPSRRF |
|  | 20 | 172-191 | NNPFYFPSRRFSTRYGNQNG |
|  | 21 | 181-200 | RFSTRYGNQNGRIRVLQRFD |
| 4 | 22 | 190-209 | NGRIRVLQREDQRSRQFQNL |
|  | 23 | 199-218 | FDQRSRQFQNLQNHRIVQIE |
|  | 24 | 208-227 | NLQNHRIVQIEAKPNTLVLP |
|  | 25 | 217-236 | IEAKPNTLVLPKHADADNIL |
|  | 26 | 226-245 | LPKHADADNILVIQQGQATV |
|  | 27 | 235-254 | ILVIQQGQATVTVANGNNRK |
|  | 28 | 244-263 | TVTVANGNNRKSFNLDEGHA |
| 5 | 29 | 253-272 | RKSFNLDEGHALRIPSGFIS |
|  | 30 | 262-281 | HALRIPSGFISYILNRHDNQ |
|  | 31 | 271-290 | ISYILNRHDNQNLRVAKISM |
|  | 32 | 280-299 | NQNLRVAKISMPVNTPGQFE |
|  | 33 | 289-308 | SMPVNTPGQFEDFFPASSRD |
|  | 34 | 298-317 | FEDFFPASSRDQSSYLQGFS |
|  | 35 | 307-326 | RDQSSYLQGFSRNTLEAAFN |
| 6 | 36 | 316-335 | FSRNTLEAAFNAEFNEIRRV |
|  | 37 | 325-344 | FNAEFNEIRRVLLEENAGGE |
|  | 38 | 334-353 | RVLLEENAGGEQEERGQRRW |
|  | 39 | 343-362 | GEQEERGQRRWSTRSSENNE |
|  | 40 | 352-371 | RWSTRSSENNEGVIVKVSKE |
|  | 41 | 361-380 | NEGVIVKVSKEHVEELTKHA |
|  | 42 | 370-389 | KEHVEELTKHAKSVSKKGSE |
| 7 | 43 | 379-398 | HAKSVSKKGSEEEGDITNPI |
|  | 44 | 388-407 | SEEEGDITNPINLREGEPDL |
|  | 45 | 397-416 | PINLREGEPDLSNNFGKLFE |
|  | 46 | 406-425 | DLSNNFGKLFEVKPDKKNPQ |
|  | 47 | 415-434 | FEVKPDKKNPQLQDLDMMLT |
|  | 48 | 424-443 | PQLQDLDMMLTCVEIKEGAL |
|  | 49 | 433-452 | LTCVEIKEGALMLPHFNSKA |
| 8 | 50 | 442-461 | ALMLPHFNSKAMVIVVVNKG |
|  | 51 | 451-470 | KAMVIVVVNKGTGNLELVAV |
|  | 52 | 460-479 | KGTGNLELVAVRKEQQQRGR |
|  | 53 | 469-488 | AVRKEQQQRGRREEEEDEDE |
|  | 54 | 478-497 | GRREEEEDEDEEEEGSNREV |
|  | 55 | 487-506 | DEEEEGSNREVRRYTARLKE |
|  | 56 | 496-515 | EVRRYTARLKEGDVFIMPAA |
| 9 | 57 | 505-524 | KEGDVFIMPAAHPVAINASS |
|  | 58 | 514-533 | AAHPVAINASSELHLLGFGI |
|  | 59 | 523-542 | SSELHLLGFGINAENNHRIF |
|  | 60 | 532-551 | GINAENNHRIFLAGDKDNVI |
|  | 61 | 541-560 | IFLAGDKDNVIDQIEKQAKD |
|  | 62 | 550-569 | VIDQIEKQAKDLAFPGSGEQ |
|  | 63 | 559-578 | KDLAFPGSGEQVEKLIKNQK |
| 10 | 64 | 568-587 | EQVEKLIKNQKESHIVSARP |
|  | 65 | 577-596 | QKESHIVSARPQSQSQSPSS |
|  | 66 | 586-605 | RPQSQSQSPSSPEKESPEKE |
|  | 67 | 595-614 | SSPEKESPEKEDQEEENQGG |
|  | 68 | 604-623 | KEDQEEENQGGKGPLLSILK |
|  | 69 | 607-626 | QEEENQGGKGPLLSILKAFN |

BIBLIOGRAPHY

Akdis and Akdis. *J Allergy Clin Immunol* 2011; 127(1):18-27; quiz 8-9.
Akdis et al., *Allergy* 55: 522-530, 2000
Akdis et al., *Trends Immunol* 22: 175-8, 2001
Alexander et al. *Allergy.* 2005; 60(10):1269-74.
Alexander et al. *Clin Exp Allergy.* 2005; 35(1):52-8.
Allen and O'Hehir. *Clin Exp Allergy.* 2011; 41(9):1172-4.
Allergen Nomenclature, International Union of Immunological Societies (LUIS) Allergen Nomenclature Subcommittee. Available at: http://www.allergen.org/Allergen.aspx. Accessed Apr. 22, 2012.
Amann et al., 1998, *Gene.*, 69:301-315
Anagnostou et al. *Clin Exp Allergy.* 2011; 41(9):1273-81.
Asarnoj et al. *Allergy.* 2010, 65(9):1189-95
Asarnoj et al. *Allergy.* 65(9):1189-95, 2010.
Avery et al. *Pediatr Allergy Immunol* 2003; 14(5):378-82.
Balderi et al., 1987, *Embo J.*, 6: 229-234)
Bateman et al. *Clin Exp Allergy.* 2008; 38(11):1760-8.
Blanc et al. *Clin Exp Allergy.* 2009; 39(8):1277-85
Bock et al. *J Allergy Clin Immunol.* 2007; 119(4):1016-8.
Boumiza et al. *Clin Mol Allergy.* 2005; 3:9.
Burks A W. *Lancet.* 2008; 371(9623):1538-46.
Burks et al. *Eur J Biochem.* 1997; 245(2):334-9.
Burks et al., *Allergy* 53: 725-30, 1998
Busse et al. *N Engl J Med.* 2002; 347(19):1535-6.
Campbell et al. *J Exp Med.* 2009; 206(7):1535-47.
Chiang et al. *Pediatr Allergy Immunol.* 2009; 21(2 Pt 2):e429-38
de Jong et al., *Clin Exp Allergy* 28: 743-51, 1998
de Leon et al. *Clin Exp Allergy.* 2003; 33(9):1273-80.
de Leon et al. *Expert Reviews in Molecular Medicine.* 2007; 9(1):1-18.
DeLong et al. *J Allergy Clin Immunol.* 2011; 127(5):1211-8 e3.
Drew et al. *J Immunol.* 2004; 173(9):5872-9.
Eusebius et al. *Int Arch Allergy Immunol.* 2002; 127(3):234-44.
Glaumann et al. *Allergy.* 2012; 67(2):242-7
Hall et al. *Vaccine.* 2003; 21(5-6):549-61.
Hemmer et al. *Int Immunol.* 2000; 12(3):375-83.
Higgins et al. *J Allergy Clin Immunol.* 1994; 93(5):891-9.
Hofmann et al. *J Allergy Clin Immunol.* 2009; 124(2):286-91.
Hourihane et al., *J Allergy Clin Immunol* 100: 596-600, 1997
Hoyne et al. *J Exp Med.* 1993; 178(5):1783-8.
Husain and Schwartz. *J Am Acad Dermatol.* 2012; 66(1): 136-43.
Jameel et al., 1990, *J. Virol.*, 64:3963-3966
Jones et al. *J Allergy Clin Immunol* 2009; 124(2):292-300.
Kammerer et al. *J Allergy Clin Immunol.* 1997; 100(1):96-103.
Kay and Larche. *Springer Semin Immunopathol.* 2004; 25(3-4):391-9.
Kemp and Hu. *Med J Aust.* 2008; 188(9):503-4.
Knapp et al., 1990, *Bio Techniques.*, 8:280-281
Koppelman et al. *Allergy.* 2001; 56(2):132-7
Koppelman et al. *Clin Exp Allergy.* 2004; 34(4):583-90
Kurjan and Herskowitz., 1982, *Cell.*, 30:933-943
Larche M. *Clin Exp Allergy.* 2008; 38(11):1709-11.
Lin et al. *J Microbiol Immunol* Infect. 2012
Lin et al. *J Microbiol Immunol Infect.* 2012.
Litwin et al., *Int Arch Allergy Appl Immunol* 87: 361-61, 998
Maguire et al., *Clin Immunol* 93: 222-31, 1999
Mannering et al. *J Immunol Methods.* 2005; 298(1-2):83-92.
Marazuela et al. *Mol Immunol.* 2008; 45(2):438-45.

Marcotte et al., *J Allergy Clin Immunol* 101: 506-13, 1998
Middleton et al. New allele frequency database: http://www.allelefrequencies.net. Tissue Antigens. 2003; 61(5):403-7.
Moverare et al. *Int Arch Allergy Immunol* 2011; 156(3):282-90
Muller et al. *J Allergy Clin Immunol* 1998; 101(6 Pt 1):747-54.
Muller et al., *J Allergy Clin Immunol* 101: 747-754, 1998
Nelson et al. *J Allergy Clin Immunol* 1997; 99(6 Pt 1):744-51.
Norman et al., *Am J Respir Crit Care Med* 154: 1623-8, 1996
Oldfield et al. *Lancet.* 2002; 360(9326):47-53.
Oppenheimer et al. *J Allergy Clin Immunol* 1992; 90(2):256-62.
Palmer and Burks. *Curr Opin Allergy Clin Immunol* 2006; 6(3):202-6.
Palmer et al. *Clin Immunol.* 2005; 115(3):302-12
Peeters et al. *Clin Exp Allergy.* 2007; 37(1):108-15
Pene et al., *J Allergy Clin Immunol* 102: 571-8, 1998
Pomés et al. 2006, *Clin. Exp. Allergy* 36(6):824-30
Prickett et al. *J Allergy Clin Immunol.* 2011; 127(3):608-15 e1-5.
Primeau et al., *Clin Exp Allergy* 30: 1135-43, 2000
Pumphrey R. *Current Opinion in Allergy & Clinical Immunology.* 2004; 4(4):285-90.
Robinson, *Br Med Bull* 56: 956-968, 2000
Rolland et al. *Curr Opin Allergy Clin Immunol.* 2010; In press.
Rolland et al. *Pharmacol Ther.* 2009; 121(3):273-84.
Ruiter et al. *Int Arch Allergy Immunol.* 2007; 143(2):119-26.
Rupa and Mine. *Allergy.* 2012; 67(1):74-82.
Sabatos-Peyton et al. *Curr Opin Immunol* 2010; 22(5):609-15.
Sampson et al., *N Engl J Med* 327: 380-4, 1992
Sampson et al. *J Allergy Clin Immunol.* 2006; 117(6):1440-5.
Schultz et al., 1987, *Gene.,* 54:113-123
Shek et al. *J Allergy Clin Immunol.* 2010; 126(2):324-31 e7.
Shreffler et al. *Ann Allergy Asthma Immunol* 2006; 96(6):865-9.
Shreffler et al. *J Allergy Clin Immunol.* 2004; 113(4):776-82.
Sicher et al., *J Allergy Clin Immunol* 103: 559-562, 1999
Sicherer et al. *J Allergy Clin Immunol.* 2010; 125(6):1322-6.
Sicherer et al., *Paediatrics* 102: e6, 1998
Singh et al. *Bioinformatics.* 2001; 17(12):1236-7.
Suri et al. *Curr Opin Immunol.* 2006; 18(1):70-7.
Thyagarajan et al. *J Allergy Clin Immunol* 2010; 126(1):31-2.
van Boxtel et al. *J Agric Food Chem.* 2008; 56(6):2223-30.
van Neerven et al. *J Immunol* 1994; 152(8):4203-10.
Varney et al. 1991 *British Medical Journal* 302:265-269
Varshney et al. *J Allergy Clin Immunol* 2009; 124(6):1351-2.
Varshney et al. *J Allergy Clin Immunol* 2011; 127(3):654-60.
Verhoef et al. *Int Immunol.* 1993; 5(12):1589-97.
Vita et al. *Nucleic Acids Res.* 2010; 38 (Database issue):D854-62.
Yang et al. *Clin Exp Allergy.* 2010; 40(4):668-78.
Yoshitomi et al. *J Pept Sci.* 2007; 13(8):499-503.
Yun and Katelaris. *Intern Med J.* 2009; 39(7):475-8.

The invention claimed is:

1. A method for reducing the severity of Ara h 1 hypersensitivity or sensitivity in a subject to an allergen present in a composition which comprises Ara h 1, said method comprising administering to said subject an effective amount of a composition comprising one or more peptides, wherein each of said one or more peptides is no more than 28 amino acids in length, wherein at least one peptide of said one or more peptides comprises VEIKEGALMLPHFNSKA (SEQ ID NO: 23), and wherein the at least one peptide does not cross-link IgE, thereby reducing the severity of Ara h 1 hypersensitivity or sensitivity to an allergen present in the composition which comprises Ara h 1 in the subject.

2. The method according to claim 1, wherein said method reduces the severity of Ara h 1 hypersensitivity in the subject to peanuts or tree nuts which contain Ara h 1.

3. The method according to claim 1, wherein said method desensitises or induces immunological tolerance to Ara h 1.

4. The method according to claim 3 wherein said desensitization or tolerance is achieved by inducing Th2 anergy or apoptosis.

5. The method according to claim 1, wherein the composition comprising one or more peptides further comprises one or more pharmaceutically acceptable carriers and/or diluents.

6. The method according to claim 1 wherein at least one additional peptide of the one or more peptides comprises a sequence selected from the group consisting of:

(i) FQNLQNHR; (SEQ ID NO: 1)

(ii) IVQIEA; (SEQ ID NO: 2)

(iii) NEGVIVKVSK; (SEQ ID NO: 3)

(iv) FGKLFEVK; (SEQ ID NO: 4)

(v) EVKPDKKNPQLQ; (SEQ ID NO: 5)

(vi) PHFNSKAMVIV; (SEQ ID NO: 7)

(vii) IVVVN; (SEQ ID NO: 8)

(viii) VVNKGTGNLEL; (SEQ ID NO: 9)
and (ix) IMPAAHP. (SEQ ID NO: 10)

7. The method according to claim 1, wherein the at least one peptide comprising VEIKEGALMLPHFNSKA (SEQ ID NO: 23) is no more than 20 amino acids in length.

8. The method according to claim 6, wherein the at least one additional peptide further comprises a sequence selected from the group consisting of:

(i) FQNLQNHRIV; (SEQ ID NO: 12)

(ii) RIVQIEAKPNTLV; (SEQ ID NO: 13)

(iii) FQNLQNHRIVQIEAKPNTLV; (SEQ ID NO: 14)

(iv) WSTRSSENNEGVIVKVSKE; (SEQ ID NO: 15)

(v) STRSSENNEGVIVKVSKE; (SEQ ID NO: 16)

(vi) ENNEGVIVKVSKE; (SEQ ID NO: 17)

(vii) NNFGKLFEVKPDKKNPQ; (SEQ ID NO: 18)

(viii) SNNFGKLFEVKPDKKNPQ; (SEQ ID NO: 19)

(ix) EVKPDKKNPQLQ; (SEQ ID NO: 20)

(x) NNFGKLFEVKPDKKNPQLQ; (SEQ ID NO: 21)

(xi) SNNFGKLFEVKPDKKNPQLQ; (SEQ ID NO: 22)

(xii) ALMLPHFNSKAMVIVVV; (SEQ ID NO: 24)

(xiii) KAMVIVVVNKG; (SEQ ID NO: 25)

(xiv) AMVIVVVNKGTGNLELVAV; (SEQ ID NO: 26)

(xv) VVNKGTGNLELVAVRK; (SEQ ID NO: 27)

(xvi) AMVIVVVNKGTGNLELV; (SEQ ID NO: 28)

(xvii) KAMVIVVVNKGTGNLELVAV; (SEQ ID NO: 29)

(xviii) GDVFIMPAAHPVAINASS; (SEQ ID NO: 30)

(xix) VFIMPAAHPVAINASSE; (SEQ ID NO: 31)

(xx) GDVFIMPAAHPVAINASSE; (SEQ ID NO: 32)
and (xxi) VFIMPAAHPVAINASS. (SEQ ID NO: 33)

(xviii) GDVFIMPAAHPVAINASS (SEQ ID NO: 30);
(xix) VFIMPAAHPVAINASSE (SEQ ID NO: 31);
(xx) GDVFIMPAAHPVAINASSE (SEQ ID NO: 32); and
(xxi) VFIMPAAHPVAINASS (SEQ ID NO: 33).

9. The method according to claim 6, wherein said one or more peptides are capable of modifying T cell function when presented to T cells isolated from subjects having an Ara h 1 hypersensitivity or sensitivity to an allergen present in a composition which comprises Ara h 1 and wherein the peptides do not 10. The method according to claim 6, wherein the at least one additional peptide comprises a sequence selected from the group consisting of:

(i)
FQNLQNHR; (SEQ ID NO: 1)

(ii)
IVQIEA; (SEQ ID NO: 2)

(iii)
NEGVIVKVSK; (SEQ ID NO: 3)

(iv)
EVKPDKKNPQLQ; (SEQ ID NO: 5)
and (v)
IMPAAHP. (SEQ ID NO: 10)

11. The method according to claim 6, wherein the at least one additional peptide comprises one or more additional peptides, together comprising each of the following sequences:

(i)
FQNLQNHR; (SEQ ID NO: 1)

(ii)
IVQIEA; (SEQ ID NO: 2)

(iii
NEGVIVKVSK; (SEQ ID NO: 3)

(iv)
EVKPDKKNPQLQ; (SEQ ID NO: 5)
and (v)
IMPAAHP. (SEQ ID NO: 10)

12. The method according to claim 1, wherein the at least one peptide does not cross-link cell-bound IgE.

13. A method for reducing the severity of Ara h 1 hypersensitivity or sensitivity in a subject to an allergen present in a composition which comprises Ara h 1, said method comprising administering to said subject an effective amount of a composition comprising one or more peptides, wherein each of said one or more peptides is no more than 28 amino acids in length, and wherein at least one peptide of said one or more peptides is identical to a fragment of Ara h 1 and comprises EGALML (SEQ ID NO: 6), thereby reducing the severity of Ara h 1 hypersensitivity or sensitivity to an allergen present in the composition which comprises Ara h 1 in the subject.

14. The method according to claim 13, wherein the at least one peptide comprising EGALML (SEQ ID NO: 6) is no more than 20 amino acids in length.

15. The method according to claim 13, wherein at least one additional peptide of the one or more peptides comprises a sequence selected from the group consisting of:

(i)
FQNLQNHR; (SEQ ID NO: 1)

(ii)
IVQIEA; (SEQ ID NO: 2)

(iii)
NEGVIVKVSK; (SEQ ID NO: 3)

(iv)
FGKLFEVK; (SEQ ID NO: 4)

(v)
EVKPDKKNPQLQ; (SEQ ID NO: 5)

(vi)
PHFNSKAMVIV; (SEQ ID NO: 7)

(vii)
IVVVN; (SEQ ID NO: 8)

(viii)
VVNKGTGNLEL; (SEQ ID NO: 9)
and (ix)
IMPAAHP. (SEQ ID NO: 10)

16. The method according to claim 15, wherein the at least one additional peptide comprises a sequence selected from the group consisting of:

(i)
FQNLQNHR; (SEQ ID NO: 1)

(ii)
IVQIEA; (SEQ ID NO: 2)

(iii)
NEGVIVKVSK; (SEQ ID NO: 3)

(iv)
EVKPDKKNPQLQ; (SEQ ID NO: 5)
and (v)
IMPAAHP. (SEQ ID NO: 10)

17. The method according to claim 15, wherein the at least one additional peptide comprises one or more additional peptides, together comprising each of the following sequences:

(i)
FQNLQNHR; (SEQ ID NO: 1)

(ii)
IVQIEA; (SEQ ID NO: 2)

-continued (iii) (SEQ ID NO: 3)
NEGVIVKVSK;

(iv) (SEQ ID NO: 5)
EVKPDKKNPQLQ;
and (v) (SEQ ID NO: 10)
IMPAAHP.

18. The method according to claim 15, wherein the at least one additional peptide further comprises a sequence selected from the group consisting of:

(i) (SEQ ID NO: 12)
FQNLQNHRIV;

(ii) (SEQ ID NO: 13)
RIVQIEAKPNTLV;

(iii) (SEQ ID NO: 14)
FQNLQNHRIVQIEAKPNTLV;

(iv) (SEQ ID NO: 15)
WSTRSSENNEGVIVKVSKE;

(v) (SEQ ID NO: 16)
STRSSENNEGVIVKVSKE;

(vi) (SEQ ID NO: 17)
ENNEGVIVKVSKE;

(vii) (SEQ ID NO: 18)
NNFGKLFEVKPDKKNPQ;

(viii) (SEQ ID NO: 19)
SNNFGKLFEVKPDKKNPQ;

(ix) (SEQ ID NO: 20)
EVKPDKKNPQLQ;

(x) (SEQ ID NO: 21)
NNFGKLFEVKPDKKNPQLQ;

(xi) (SEQ ID NO: 22)
SNNFGKLFEVKPDKKNPQLQ;

(xii) (SEQ ID NO: 24)
ALMLPHFNSKAMVIVVV;

(xiii) (SEQ ID NO: 25)
KAMVIVVVNKG;

(xiv) (SEQ ID NO: 26)
AMVIVVVNKGTGNLELVAV;

(xv) (SEQ ID NO: 27)
VVNKGTGNLELVAVRK;

(xvi) (SEQ ID NO: 28)
AMVIVVVNKGTGNLELV;

(xvii) (SEQ ID NO: 29)
KAMVIVVVNKGTGNLELVAV;

(xviii) (SEQ ID NO: 30)
GDVFIMPAAHPVAINASS;

(xix) (SEQ ID NO: 31)
VFIMPAAHPVAINASSE;

(xx) (SEQ ID NO: 32)
GDVFIMPAAHPVAINASSE;
and (xxi) (SEQ ID NO: 33)
VFIMPAAHPVAINASS.

\* \* \* \* \*

```
                        SEQUENCE LISTING

<160> NUMBER OF SEQ ID NOS: 33

<210> SEQ ID NO 1
<211> LENGTH: 8
<212> TYPE: PRT
<213> ORGANISM: Artificial Sequence
<220> FEATURE:
<223> OTHER INFORMATION: chemically synthezised

<400> SEQUENCE: 1

Phe Gln Asn Leu Gln Asn His Arg
1               5

<210> SEQ ID NO 2
<211> LENGTH: 6
<212> TYPE: PRT
<213> ORGANISM: Artificial Sequence
<220> FEATURE:
<223> OTHER INFORMATION: chemically synthezised

<400> SEQUENCE: 2

Ile Val Gln Ile Glu Ala
1               5

<210> SEQ ID NO 3
<211> LENGTH: 10
<212> TYPE: PRT
<213> ORGANISM: Artificial Sequence
<220> FEATURE:
<223> OTHER INFORMATION: chemically synthezised

<400> SEQUENCE: 3

Asn Glu Gly Val Ile Val Lys Val Ser Lys
1               5                   10
```

<210> SEQ ID NO 4
<211> LENGTH: 8
<212> TYPE: PRT
<213> ORGANISM: Artificial Sequence
<220> FEATURE:
<223> OTHER INFORMATION: Chemically synthezised

<400> SEQUENCE: 4

Phe Gly Lys Leu Phe Glu Val Lys
1               5

<210> SEQ ID NO 5
<211> LENGTH: 12
<212> TYPE: PRT
<213> ORGANISM: Artificial Sequence
<220> FEATURE:
<223> OTHER INFORMATION: Chemically synthezised

<400> SEQUENCE: 5

Glu Val Lys Pro Asp Lys Lys Asn Pro Gln Leu Gln
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Chemically synthezised

<400> SEQUENCE: 6

Glu Gly Ala Leu Met Leu
1               5

<210> SEQ ID NO 7
<211> LENGTH: 11
<212> TYPE: PRT
<213> ORGANISM: Artificial Sequence
<220> FEATURE:
<223> OTHER INFORMATION: Chemically Synthezised

<400> SEQUENCE: 7

Pro His Phe Asn Ser Lys Ala Met Val Ile Val
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Chemically synthezised

<400> SEQUENCE: 8

Ile Val Val Val Asn
1               5

<210> SEQ ID NO 9
<211> LENGTH: 11
<212> TYPE: PRT
<213> ORGANISM: Artificial Sequence
<220> FEATURE:
<223> OTHER INFORMATION: Chemically Synthezised

<400> SEQUENCE: 9

Val Val Asn Lys Gly Thr Gly Asn Leu Glu Leu
1               5                   10

```
<210> SEQ ID NO 10
<211> LENGTH: 7
<212> TYPE: PRT
<213> ORGANISM: Artificial Sequence
<220> FEATURE:
<223> OTHER INFORMATION: Chemically Synthezised

<400> SEQUENCE: 10

Ile Met Pro Ala Ala His Pro
1               5

<210> SEQ ID NO 11
<211> LENGTH: 626
<212> TYPE: PRT
<213> ORGANISM: Homo sapiens

<400> SEQUENCE: 11

Met Arg Gly Arg Val Ser Pro Leu Met Leu Leu Leu Gly Ile Leu Val
1               5                   10                  15

Leu Ala Ser Val Ser Ala Thr His Ala Lys Ser Ser Pro Tyr Gln Lys
                20                  25                  30

Lys Thr Glu Asn Pro Cys Ala Gln Arg Cys Leu Gln Ser Cys Gln Gln
            35                  40                  45

Glu Pro Asp Asp Leu Lys Gln Lys Ala Cys Glu Ser Arg Cys Thr Lys
        50                  55                  60

Leu Glu Tyr Asp Pro Arg Cys Val Tyr Asp Pro Arg Gly His Thr Gly
65                  70                  75                  80

Thr Thr Asn Gln Arg Ser Pro Gly Glu Arg Thr Arg Gly Arg Gln
                85                  90                  95

Pro Gly Asp Tyr Asp Asp Arg Arg Gln Pro Arg Arg Glu Glu Gly
                100                 105                 110

Gly Arg Trp Gly Pro Ala Gly Pro Arg Glu Arg Glu Arg Glu Glu Asp
            115                 120                 125

Trp Arg Gln Pro Arg Glu Asp Trp Arg Pro Ser His Gln Gln Pro
        130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
    290                 295                 300

Ser Ser Arg Asp Gln Ser Ser Tyr Leu Gln Gly Phe Ser Arg Asn Thr
```

-continued

```
             305                 310                 315                 320
        Leu Glu Ala Ala Phe Asn Ala Glu Phe Asn Glu Ile Arg Arg Val Leu
                        325                 330                 335
        Leu Glu Glu Asn Ala Gly Gly Glu Gln Glu Glu Arg Gly Gln Arg Arg
                        340                 345                 350
        Trp Ser Thr Arg Ser Ser Glu Asn Glu Gly Val Ile Val Lys Val
                        355                 360                 365
        Ser Lys Glu His Val Glu Leu Thr Lys His Ala Lys Ser Val Ser
                    370                 375                 380
        Lys Lys Gly Ser Glu Glu Gly Asp Ile Thr Asn Pro Ile Asn Leu
        385                 390                 395                 400
        Arg Glu Gly Glu Pro Asp Leu Ser Asn Asn Phe Gly Lys Leu Phe Glu
                            405                 410                 415
        Val Lys Pro Asp Lys Lys Asn Pro Gln Leu Gln Asp Leu Asp Met Met
                        420                 425                 430
        Leu Thr Cys Val Glu Ile Lys Glu Gly Ala Leu Met Leu Pro His Phe
                        435                 440                 445
        Asn Ser Lys Ala Met Val Ile Val Val Asn Lys Gly Thr Gly Asn
                    450                 455                 460
        Leu Glu Leu Val Ala Val Arg Lys Glu Gln Gln Gln Arg Gly Arg Arg
        465                 470                 475                 480
        Glu Glu Glu Glu Asp Glu Asp Glu Glu Glu Gly Ser Asn Arg Glu
                        485                 490                 495
        Val Arg Arg Tyr Thr Ala Arg Leu Lys Glu Gly Asp Val Phe Ile Met
                        500                 505                 510
        Pro Ala Ala His Pro Val Ala Ile Asn Ala Ser Ser Glu Leu His Leu
                        515                 520                 525
        Leu Gly Phe Gly Ile Asn Ala Glu Asn Asn His Arg Ile Phe Leu Ala
                    530                 535                 540
        Gly Asp Lys Asp Asn Val Ile Asp Gln Ile Glu Lys Gln Ala Lys Asp
        545                 550                 555                 560
        Leu Ala Phe Pro Gly Ser Gly Glu Gln Val Glu Lys Leu Ile Lys Asn
                        565                 570                 575
        Gln Lys Glu Ser His Phe Val Ser Ala Arg Pro Gln Ser Gln Ser Gln
                        580                 585                 590
        Ser Pro Ser Pro Glu Lys Glu Ser Pro Glu Lys Glu Asp Gln Glu
                    595                 600                 605
        Glu Glu Asn Gln Gly Gly Lys Gly Pro Leu Leu Ser Ile Leu Lys Ala
        610                 615                 620
        Phe Asn
        625

<210> SEQ ID NO 12
<211> LENGTH: 10
<212> TYPE: PRT
<213> ORGANISM: Artificial Sequence
<220> FEATURE:
<223> OTHER INFORMATION: Chemically synthezised

<400> SEQUENCE: 12

Phe Gln Asn Leu Gln Asn His Arg Ile Val
1               5                   10

<210> SEQ ID NO 13
<211> LENGTH: 13
<212> TYPE: PRT
```

-continued

```
<213> ORGANISM: Artificial Sequence
<220> FEATURE:
<223> OTHER INFORMATION: Chemically synthezised

<400> SEQUENCE: 13

Arg Ile Val Gln Ile Glu Ala Lys Pro Asn Thr Leu Val
1               5                   10

<210> SEQ ID NO 14
<211> LENGTH: 20
<212> TYPE: PRT
<213> ORGANISM: Artificial Sequence
<220> FEATURE:
<223> OTHER INFORMATION: Chemically synthezised

<400> SEQUENCE: 14

Phe Gln Asn Leu Gln Asn His Arg Ile Val Gln Ile Glu Ala Lys Pro
1               5                   10                  15

Asn Thr Leu Val
            20

<210> SEQ ID NO 15
<211> LENGTH: 19
<212> TYPE: PRT
<213> ORGANISM: Artificial Sequence
<220> FEATURE:
<223> OTHER INFORMATION: Chemically Synthezised

<400> SEQUENCE: 15

Trp Ser Thr Arg Ser Ser Glu Asn Asn Glu Gly Val Ile Val Lys Val
1               5                   10                  15

Ser Lys Glu

<210> SEQ ID NO 16
<211> LENGTH: 18
<212> TYPE: PRT
<213> ORGANISM: Artificial Sequence
<220> FEATURE:
<223> OTHER INFORMATION: Chemically synthezised

<400> SEQUENCE: 16

Ser Thr Arg Ser Ser Glu Asn Asn Glu Gly Val Ile Val Lys Val Ser
1               5                   10                  15

Lys Glu

<210> SEQ ID NO 17
<211> LENGTH: 13
<212> TYPE: PRT
<213> ORGANISM: Artificial Sequence
<220> FEATURE:
<223> OTHER INFORMATION: Chemically synthezised

<400> SEQUENCE: 17

Glu Asn Asn Glu Gly Val Ile Val Lys Val Ser Lys Glu
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Chemically synthezised

<400> SEQUENCE: 18

Asn Asn Phe Gly Lys Leu Phe Glu Val Lys Pro Asp Lys Lys Asn Pro
```

```
1               5                   10                  15
Gln

<210> SEQ ID NO 19
<211> LENGTH: 18
<212> TYPE: PRT
<213> ORGANISM: Artificial Sequence
<220> FEATURE:
<223> OTHER INFORMATION: Chemically synthezised

<400> SEQUENCE: 19

Ser Asn Asn Phe Gly Lys Leu Phe Glu Val Lys Pro Asp Lys Lys Asn
1               5                   10                  15

Pro Gln

<210> SEQ ID NO 20
<211> LENGTH: 12
<212> TYPE: PRT
<213> ORGANISM: Artificial Sequence
<220> FEATURE:
<223> OTHER INFORMATION: Chemically synthezised

<400> SEQUENCE: 20

Glu Val Lys Pro Asp Lys Lys Asn Pro Gln Leu Gln
1               5                   10

<210> SEQ ID NO 21
<211> LENGTH: 19
<212> TYPE: PRT
<213> ORGANISM: Artificial Sequence
<220> FEATURE:
<223> OTHER INFORMATION: Chemcially synthezised

<400> SEQUENCE: 21

Asn Asn Phe Gly Lys Leu Phe Glu Val Lys Pro Asp Lys Lys Asn Pro
1               5                   10                  15

Gln Leu Gln

<210> SEQ ID NO 22
<211> LENGTH: 20
<212> TYPE: PRT
<213> ORGANISM: Artificial Sequence
<220> FEATURE:
<223> OTHER INFORMATION: Chemically synthezised

<400> SEQUENCE: 22

Ser Asn Asn Phe Gly Lys Leu Phe Glu Val Lys Pro Asp Lys Lys Asn
1               5                   10                  15

Pro Gln Leu Gln
            20

<210> SEQ ID NO 23
<211> LENGTH: 17
<212> TYPE: PRT
<213> ORGANISM: Artificial Sequence
<220> FEATURE:
<223> OTHER INFORMATION: Chemcially synthezised

<400> SEQUENCE: 23

Val Glu Ile Lys Glu Gly Ala Leu Met Leu Pro His Phe Asn Ser Lys
1               5                   10                  15

Ala
```

```
<210> SEQ ID NO 24
<211> LENGTH: 17
<212> TYPE: PRT
<213> ORGANISM: Artificial Sequence
<220> FEATURE:
<223> OTHER INFORMATION: Chemcially synthezised

<400> SEQUENCE: 24

Ala Leu Met Leu Pro His Phe Asn Ser Lys Ala Met Val Ile Val Val
1               5                   10                  15

Val

<210> SEQ ID NO 25
<211> LENGTH: 11
<212> TYPE: PRT
<213> ORGANISM: Artificial Sequence
<220> FEATURE:
<223> OTHER INFORMATION: Chemcially synthezised

<400> SEQUENCE: 25

Lys Ala Met Val Ile Val Val Val Asn Lys Gly
1               5                   10

<210> SEQ ID NO 26
<211> LENGTH: 19
<212> TYPE: PRT
<213> ORGANISM: Artificial Sequence
<220> FEATURE:
<223> OTHER INFORMATION: Chemically synthezised

<400> SEQUENCE: 26

Ala Met Val Ile Val Val Val Asn Lys Gly Thr Gly Asn Leu Glu Leu
1               5                   10                  15

Val Ala Val

<210> SEQ ID NO 27
<211> LENGTH: 16
<212> TYPE: PRT
<213> ORGANISM: Artificial Sequence
<220> FEATURE:
<223> OTHER INFORMATION: Chemcially synthezised

<400> SEQUENCE: 27

Val Val Asn Lys Gly Thr Gly Asn Leu Glu Leu Val Ala Val Arg Lys
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Chemcially synthezised

<400> SEQUENCE: 28

Ala Met Val Ile Val Val Val Asn Lys Gly Thr Gly Asn Leu Glu Leu
1               5                   10                  15

Val

<210> SEQ ID NO 29
<211> LENGTH: 20
<212> TYPE: PRT
<213> ORGANISM: Artificial Sequence
<220> FEATURE:
<223> OTHER INFORMATION: Chemcially Synthezised

<400> SEQUENCE: 29
```

```
Lys Ala Met Val Ile Val Val Asn Lys Gly Thr Gly Asn Leu Glu
1               5                   10                  15

Leu Val Ala Val
            20

<210> SEQ ID NO 30
<211> LENGTH: 18
<212> TYPE: PRT
<213> ORGANISM: Artificial Sequence
<220> FEATURE:
<223> OTHER INFORMATION: Chemcially synthezised

<400> SEQUENCE: 30

Gly Asp Val Phe Ile Met Pro Ala Ala His Pro Val Ala Ile Asn Ala
1               5                   10                  15

Ser Ser

<210> SEQ ID NO 31
<211> LENGTH: 17
<212> TYPE: PRT
<213> ORGANISM: Artificial Sequence
<220> FEATURE:
<223> OTHER INFORMATION: Chemically synthezised

<400> SEQUENCE: 31

Val Phe Ile Met Pro Ala Ala His Pro Val Ala Ile Asn Ala Ser Ser
1               5                   10                  15

Glu

<210> SEQ ID NO 32
<211> LENGTH: 19
<212> TYPE: PRT
<213> ORGANISM: Artificial Sequence
<220> FEATURE:
<223> OTHER INFORMATION: Chemically synthezised

<400> SEQUENCE: 32

Gly Asp Val Phe Ile Met Pro Ala Ala His Pro Val Ala Ile Asn Ala
1               5                   10                  15

Ser Ser Glu

<210> SEQ ID NO 33
<211> LENGTH: 16
<212> TYPE: PRT
<213> ORGANISM: Artificial Sequence
<220> FEATURE:
<223> OTHER INFORMATION: Chemically synthezised

<400> SEQUENCE: 33

Val Phe Ile Met Pro Ala Ala His Pro Val Ala Ile Asn Ala Ser Ser
1               5                   10                  15
```